United States Patent
Hashiba

(10) Patent No.: US 8,852,108 B2
(45) Date of Patent: *Oct. 7, 2014

(54) ULTRASOUND IMAGING DEVICE

(75) Inventor: Kunio Hashiba, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/432,551

(22) Filed: Mar. 28, 2012

(65) Prior Publication Data

US 2012/0197126 A1    Aug. 2, 2012

Related U.S. Application Data

(63) Continuation of application No. 12/160,905, filed as application No. PCT/JP2006/325815 on Dec. 25, 2006, now Pat. No. 8,235,899.

(30) Foreign Application Priority Data

Mar. 24, 2006    (JP) .................................. 2006-082947

(51) Int. Cl.
  *A61B 8/14*    (2006.01)
  *G01S 7/52*    (2006.01)
  *G01S 15/89*    (2006.01)
  *G06T 11/00*    (2006.01)
  *A61B 8/08*    (2006.01)

(52) U.S. Cl.
  CPC .............. *G01S 7/52038* (2013.01); *A61B 8/14* (2013.01); *G01S 15/8979* (2013.01); *G06T 11/005* (2013.01); *A61B 8/5207* (2013.01); *A61B 8/5246* (2013.01); *A61B 8/488* (2013.01); *G01S 15/895* (2013.01); *G01S 15/8963* (2013.01); *Y10S 128/916* (2013.01)
  USPC ............ 600/443; 600/437; 600/447; 128/916

(58) Field of Classification Search
  None
  See application file for complete search history.

(56) References Cited

U.S. PATENT DOCUMENTS

| | | | |
|---|---|---|---|
| 6,440,075 B1 | 8/2002 | Averkiou | |
| 6,544,182 B2 | 4/2003 | Averkiou | |

(Continued)

FOREIGN PATENT DOCUMENTS

| | | |
|---|---|---|
| JP | 2002-301068 | 10/2002 |
| JP | 2004-504911 | 2/2004 |

(Continued)

OTHER PUBLICATIONS

European Communication dated Dec. 7, 2012 for Corresponding Application No. 06835185.7.

*Primary Examiner* — Long V. Le
*Assistant Examiner* — Farshad Negarestan
(74) *Attorney, Agent, or Firm* — Antonelli, Terry, Stout & Kraus, LLP.

(57) ABSTRACT

An ultrasound imaging apparatus includes a transmitter which transmits an ultrasound pulse to a subject, a receiver which receives ultrasound coming from the subject, and a signal processor to process a received signal at the receiver and generate image data. The receiver has a predetermined reception band, and the ultrasound pulse transmitted by the transmitter has one frequency band with a frequency peak. Each of an upper limit frequency and a lower limit frequency of the one frequency band is set to be values which make a low frequency harmonic component and a high frequency harmonic component produced by the ultrasound pulse be within the reception band. The signal processor generates image data by using a nonlinear component of at least one of the low frequency and high frequency harmonic component received by the receiver.

3 Claims, 17 Drawing Sheets

(56) References Cited

U.S. PATENT DOCUMENTS

| | | |
|---|---|---|
| 6,705,996 B2 | 3/2004 | Kawagishi et al. |
| 7,056,290 B2 | 6/2006 | Rielly et al. |
| 2002/0040188 A1 | 4/2002 | Averkiou |
| 2004/0254462 A1 | 12/2004 | Kawagishi et al. |
| 2005/0252295 A1 | 11/2005 | Fink et al. |
| 2006/0036169 A1* | 2/2006 | Satoh .......................... 600/437 |

FOREIGN PATENT DOCUMENTS

| | | |
|---|---|---|
| JP | 2004-510514 | 4/2004 |
| JP | 2004-298620 | 10/2004 |
| JP | 2006-500089 | 1/2006 |
| WO | WO 02/10795 A2 | 2/2002 |
| WO | WO 02/29433 A2 | 4/2002 |
| WO | WO 2006/003556 | 1/2006 |

* cited by examiner

Figure 6

| carrier wave | $\cos 2\pi f_c t$ | $\cos 2\pi f_c t$ | $\sin 2\pi f_c t$ | $\sin 2\pi f_c t$ |
|---|---|---|---|---|
| modulating wave | $1+m\cos 2\pi f_s t$ | $1+m\sin 2\pi f_s t$ | $1+m\cos 2\pi f_s t$ | $1+m\sin 2\pi f_s t$ |
| $f_s$ component | 0 | $\pi/2$ | 0 | $\pi/2$ |
| $2f_s$ component | 0 | $\pi$ | 0 | $\pi$ |
| $2f_c - 2f_s$ component | 0 | $\pi$ | $\pi$ | 0 |
| $2f_c - f_s$ component | 0 | $-\pi/2$ | $\pi$ | $\pi/2$ |
| $2f_c$ component | 0 | 0 | $\pi$ | $\pi$ |
| $2f_c + f_s$ component | 0 | $\pi/2$ | $\pi$ | $-\pi/2$ |
| $2f_c + 2f_s$ component | 0 | $\pi$ | $\pi$ | 0 |

ULTRASOUND IMAGING DEVICE

CROSS REFERENCE TO RELATED APPLICATION

This application is a continuation application of U.S. application Ser. No. 12/160,905, filed Jul. 15, 2008, now U.S. Pat. No. 8,235,899 which application is a 371 of PCT/JP2006/325815, filed Dec. 25, 2006, the contents of which are incorporated herein by reference.

FIELD OF THE INVENTION

The present invention relates to an ultrasound imaging device used in the medical field, wherein nonlinear components generated by the acoustic nonlinear effects in the living body are used for imaging.

PRIOR ART

The ultrasound imaging device, which can visualize cross-sectional view of the living body less invasively, is used broadly for medical purposes. When the ultrasound wave is irradiated in the living body the waveform is distorted due to acoustic nonlinearity of the tissue of the living body, and nonlinear components are generated depending on the frequency components of the irradiated ultrasound waves. The imaging method using these nonlinear components is generally called as the tissue harmonic imaging (THI). For example, if the second harmonic components (or high-frequency harmonic components) surrounding the frequency $2f_0$, which are generated by the irradiation of pulse wave consisting of fundamental frequency components surrounding the frequency $f_0$, are used for imaging, the resolution is improved as compared with the imaging using the fundamental frequency components and artifacts caused by grating lobe are reduced. Consequently, the quality of the image is improved.

In the imaging method using THI, since the strength of the generated nonlinear components contained in the reflected echo is extremely smaller than the reflected fundamental frequency components, it is necessary to separate the nonlinear components from the reflected echo. Conventionally, as shown in FIG. 17, the second harmonic component was extracted by filter separating the second harmonic component, which is generated surrounding the frequency $2f_0$, and the fundamental frequency component surrounding the frequency $f_0$ from the echo.

Another method used for extracting nonlinear components contained in the echo is the pulse inversion (PI) method. FIG. 18 shows the concept of the PI method in frequency space. This method extracts nonlinear components by adding the first echo, which is obtained by transmitting the first pulse consisting of fundamental frequency components and the second echo, which is obtained by transmitting the second pulse, 180 degree-inverted phase component of the first pulse. The nonlinear component can be expressed using the square of the fundamental frequency component, and the fundamental frequency components contained in the first and second pulse echoes are offset each other but the nonlinear components remain. Accordingly, by using the PI method, though the frame rate is halved, nonlinear components can be obtained even the bands of fundamental frequency component and nonlinear component are overlapped.

As mentioned earlier, the THI using the second harmonics realizes the improved quality of image due to higher resolution and reduced artifact. However, the second harmonics have higher frequency than the fundamental wave, and therefore undergo strong frequency-dependent attenuation. Accordingly, the reduced ultrasound penetration in deep part of the imaging region makes it difficult to obtain images with uniform brightness. The patent document 1 (paragraph 0018, FIG. 6) discloses the imaging by extracting low-frequency harmonic components surrounding DC, which are generated as nonlinear components and have lower frequency than those of fundamental wave (frequency components in the band slightly expanding around the zero frequency in the center). The low-frequency harmonic components are extracted by filtration or PI method. In order for most of the low-frequency harmonic components thus extracted to be contained in the ultrasound probe-sensitive band, it has been proposed in the Patent Document 1 (paragraph 0022) that the frequency of the fundamental frequency component should agree with the highest band of the ultrasound probe-sensitive band and that the center frequency of the low-frequency harmonic components should be shifted to the slightly higher band.

Above mentioned Patent Document 1 (paragraph 0024, FIG. 8) discloses another method to generate and extract difference-frequency wave component of $f_b-f_a$, which is a kind of low-frequency harmonics, in addition to low-frequency harmonic component surrounding DC by irradiating ultrasound waves having two peaks $f_a$ and $f_b$ ($f_a<f_b$) on the frequency spectrum as a fundamental frequency component, as shown in FIG. 19. Since this method allows more low-frequency harmonic components to be contained in the probe-sensitive band, low-frequency harmonic wave components can be extracted more efficiently.

The Patent Document 2 (paragraph 0038, FIG. 2), on the other hand, discloses the method to use the components of $f_b-f_a$ and $2f_a$ for imaging by controlling the frequency and the phase of $f_b$ and superimposing the aforementioned difference-frequency wave components of $f_b-f_a$ on the components $2f_a$. According to this method, nonlinear components of wider band than the frequency band which has been used conventionally in the THI can be extracted by mutually controlling harmonics component $2f_a$ and difference-frequency wave components $f_b-f_a$.

[Patent Document 1]
Japan Published unexamined patents application No. 2002-301068
[Patent Document 1]
Japan Published unexamined patents application No. 2004-298620

DISCLOSURE OF THE INVENTION

Object to be Achieved by the Invention

The aforementioned conventional ultrasound imaging device, which uses nonlinear components, extracts only either of the high-frequency harmonics or low-frequency harmonics components or only part of the whole nonlinear components that may be generated. In other word, as above mentioned, the conventional ultrasound imaging device, which uses low-frequency harmonics, extracts only low-frequency harmonic components. Or it extracts either of the component $2f_a$ or $f_b-f_a$ or both of them by irradiating ultrasound wave with the fundamental frequency components having a peak at two frequencies, $f_a$ and $f_b$. However, of the low-frequency harmonic components and high-frequency harmonic components, the frequency components of $2f_b$ and $f_a+f_b$ have the highest rate of energy conversion from fundamental frequency components to nonlinear frequency components.

Accordingly, in the conventional ultrasound imaging device using low-frequency harmonics many nonlinear frequency components are not used as signals for imaging.

The most effective way to increase the strength of nonlinear frequency components is to increase the strength of fundamental frequency component of the transmission pulse. However, in respect of its use for the living body, the ultrasonic strength of irradiation is specified as mechanical index (MI) for safety purpose. Therefore when ultrasonic pulse wave having fundamental frequency components with a peak at two frequencies, $f_a$ and $f_b$, is irradiated, the strength of its component $f_a$ must be lower than the strength of $f_a$ when the ultrasonic pulse wave having a frequency component of $f_a$ alone is irradiated. The nonlinear frequency component has the sound pressure amplitude, which is proportional to the square of that of the fundamental frequency component. As a result, the generation of $2f_a$ component arising as harmonic component is restrained.

As explained above, conventional ultrasound nonlinear imaging extracts only part of the nonlinear components, which are expressed by the low-frequency harmonic components and high-frequency harmonic components derived from the fundamental frequency components, and uses them for imaging. Improvement of ultrasound penetration requires higher ultrasonic energy, but the conventional imaging has a disadvantage of poor energy use efficiency.

The object of the present invention is to provide an ultrasound imaging device which can extract nonlinear frequency components efficiently and improve ultrasound penetration.

Means for Solving the Problems

According to the first embodiment of the present invention, the following ultrasound imaging device will be provided in order to solve the aforementioned problems. Namely, the ultrasound imaging device has a transmitting means which transmits ultrasound wave to the target, a receiving means which receives ultrasound wave arriving from the target and a signal processor which processes signals received at the receiving means and generates image data, wherein the receiving means has a given receiving band in which the first frequency is a lower limit frequency. In this case, the frequency band of the ultrasound wave which is transmitted by the transmitting means is set at higher than the first frequency and at least three times of the first frequency. When the ultrasound wave in such band is transmitted, of all nonlinear components, the low-frequency harmonic components having a higher frequency than the first frequency can be received by the receiving means.

In the transmission by the aforementioned transmitting means, the wave whose spectral components are all cosine waves can be used. As this enables the generation of all nonlinear frequency components in-phase, the amplitudes of nonlinear components strengthen each other, thereby making it possible to obtain high-resolution image.

In the transmission by the aforementioned transmitting means, the wave whose spectral components are all sine waves can be used. As this enables the transmission of ultrasound wave with larger pulse power than that using cosine wave, the ultrasound penetration is improved.

In the transmission by the transmitting means, the ultrasound wave contains carrier wave components and modulating wave components modulating the amplitude of the carrier wave components. The carrier wave component of cosine wave can be used. The carrier wave components of sine wave can be also used.

In the transmission by the transmitting means, the ultrasound wave contains the carrier wave components and modulating wave components modulating the amplitude of the carrier wave components, wherein the carrier wave whose frequency is set as twice of the first frequency and the modulating wave whose frequency is set as the first frequency can be used. This makes it possible to set the frequency band of the ultrasound wave to be transmitted as higher than the first frequency and at least three times of the first frequency.

It can be also configured to have an accepting means to accept instructions from users to increase or decrease the frequency of the modulating wave having the first frequency at a center. In this case, the transmitting means is configured to increase or decrease the frequency of modulating wave depending on the increment or decrement accepted by the accepting means.

Also, if the upper limit frequency in the receiving band of the receiving means is the second frequency $f_2$, the frequency $f_c$ of the carrier wave and the frequency $f_s$ of modulating wave can be set to satisfy the relationship with the second frequency $f_2$ which is expressed by $2f_c+2f_s \leq f_2$. By this, it is possible to make the highest frequency of the nonlinear frequency components lower than that of the second frequency, and to receive them by the receiving means.

The aforementioned transmitting means can be configured to transmit, as the ultrasound waves, the first ultrasound wave in the aforementioned frequency band and the second ultrasound wave, which is in the aforementioned frequency band and whose waveform is the inverted one of the first ultrasound wave. The signal processor applies a so called pulse inversion method, in which the signal processor adds the first received signals, which is ultrasound wave originating from the aforementioned first ultrasound wave, coming from the aforementioned target and received by the receiving means, and the second received signals, which is ultrasound wave originating from the second ultrasound wave, coming from the target and received by the receiving means, and generates the aforementioned image data by using the added signals.

Also, according to the second embodiment of the present invention, the following ultrasound imaging device is provided. That is the ultrasound imaging device comprising a transmitting means to transmit ultrasound wave to the target, a receiving means to receive ultrasound wave from the target, and a signal processor to process the signals received by the receiving means and generate the image data, wherein the receiving means has a given receiving band in which the first frequency is the lower limit frequency. The ultrasound wave to be transmitted by the transmitting means contains carrier wave and modulating wave to modulate the carrier wave, wherein the frequency of the carrier wave is set as twice or more of the first frequency and the frequency of the modulating frequency is set as higher than the first frequency. By transmitting the ultrasound wave in such band, of the nonlinear frequency components the low-frequency harmonic component having higher frequency than the first frequency can be received by the receiving means.

In the second embodiment, the frequency of the carrier wave can be set as twice of the first frequency, while the frequency of the modulating wave can be set as the first frequency.

In the second embodiment, if the upper limit frequency in the receiving band of the receiving means is the second frequency $f_2$, it is possible to use the frequency $f_c$ of the carrier wave and the frequency $f_s$ of the modulating wave, which have the relationship with the aforementioned second frequency $f_2$ to be expressed as $2f_c+2f_s \leq f_2$. By this, it is possible to make the highest frequency of the nonlinear frequency components lower than that of the second frequency, and to receive them by the receiving means.

In the second embodiment, the ultrasound wave whose spectral components are all cosine or sine waves can be used as the ultrasound wave which is transmitted by the transmitting means. If all of the components are cosine waves, the amplitudes of the nonlinear components strengthen each other and provide a high resolution image. If all of the components are sine waves, the ultrasound wave with high pulse power can be transmitted, and consequently the ultrasound penetration is improved.

In the second embodiment, the frequency of the modulating wave can be configured to contain the means to accept instructions from users to increase or decrease the frequency of the modulating wave from the aforementioned first frequency. In this case, the transmitting means is equipped with a frequency adjusting means which increases or decreases the frequency of the modulating wave depending on the increment or decrement accepted by the aforementioned accepting means.

In the second embodiment, the pulse inversion method can be applied in which the transmitting means transmits, as ultrasound wave, the first ultrasound wave and the second ultrasound wave having the inverted waveform of the aforementioned first ultrasound wave.

Effect of the Invention

According to the present invention, since various low-frequency harmonic components and high-frequency harmonic components are generated effectively in the probe-sensitive band by the nonlinear acoustic interaction of the components in the band of transmission pulse, nonlinear imaging with high energy-use efficiency is provided. As a result, high-resolution imaging using a wider band is achieved in the shallow part of the imaging region where the level of high frequency components in the nonlinear components is relatively high and in the region close to the transmission focal point. And, even in the deep part of the imaging region where high frequency components attenuate, sufficient penetration is obtained by the imaging with low frequency components. Consequently, a uniform image over the entire imaging region can be obtained.

BEST MODE FOR CARRYING OUT THE INVENTION

Embodiments of the present invention will be explained below with reference to the attached drawings.

The embodiment of this invention is an ultrasound imaging device using nonlinear components, and has a configuration to produce low-frequency harmonic components and high-frequency harmonic components at the same time in the probe-sensitive band. This enables the probe to detect many of the nonlinear components, thereby improving energy-use efficiency and the ultrasound penetration.

To begin with, the ultrasound imaging device of this embodiment is explained by using FIG. 1. Here, among ultrasound imaging device, particularly the ultrasound diagnostic equipment 10 used for medical purpose is explained, but the ultrasound imaging device of the present invention is not limited to the diagnostic apparatus for the medical purposes.

The ultrasound diagnostic equipment 10 is equipped with a probe 11, a main frame 20, and an outer interface 12 and a display 13.

In transmission, the probe 11 converts transmission electric signals from the main frame 20 into transmission echo signals, and after transmitting the ultrasound wave to the non-illustrated subjects, it converts the echo signals reflected from the subject to the reception electric signals and transmit them to the main frame 20. The probe 11 usually has one- or two-dimensional array structure, which is configured to enable to focus and deflect the transmitted beam and received beam.

The main frame 20 comprises a pulse synchronizer 23, which generates waveform to be transmitted from the probe 11, a transmit amplifier 22, which amplifies the transmission waveform from the pulse synchronizer 23, receive amplifier 24, which amplifies signals received from the probe 11, transmit/receive (T/R) switch 21, which electrically connects the transmit amplifier 22 and the probe 11 in transmission and the receive amplifier 24 and the probe 11 in reception, the A/D converter 25, which converts analog signals amplified by the receive amplifier 24 into digital signals, receive beamformer 26, which gives a given delay to the aforementioned received signals to form received beam, a signal processor 27, which applies signal processing to the aforementioned received beam as described below in detail, an image processor 28, which constructs image data using the output from the signal processor 27, and a controller 29, which controls transmission/reception timing, transmission waveform, receive amplifier gain, amount of delay, signal processing and others for the constituent elements.

The output from the imaging processor 28 is displayed on the display 23 as an image such as 2-D tomogram and 3-D image. It is configured to enable operators to control the aforementioned constituent elements of the main frame 20 and the display 13, through the controller 29 from the outer interface 12. In addition, if the outer interface 12 is not added, imaging can be performed under the control conditions determined in advance.

Next, the action of pulse transmission and reception and the processing sequences at the signal processor 27 in the ultrasound diagnostic equipment of this invention will be explained in detail with reference to FIG. 1 and FIG. 2.

The ultrasound diagnostic equipment of the present invention uses the pulse inversion method, in which one image data can be obtained by at least two-rate transmission and reception, as shown in FIG. 1. The frequency band of the fundamental frequency components of the transmission pulse, which is a feature of the present invention, will be explained in detail later.

Firstly, a given transmission pulse waveform is formed by using the controller 29 at the pulse synchronizer 23, and via the transmit amplifier 22 and the transmit/receive switch 21, the first fundamental wave pulse 30 is irradiated from the ultrasound probe 11 onto the subject. The first fundamental wave pulse 30 propagates in the body of the subject while producing waveform distortions due to acoustic nonlinear effects and repeating reflections and penetrations in a boundary of different acoustic impedance. After the first fundamental wave pulse 30 is irradiated from the probe 11, the transmit/receive switch 21 electrically connects the receive amplifier 24 and the probe 11 immediately according to the instructions from the controller 29. The echo reflected from the subject sequentially arrives at the probe 11 as the first echo 31 in the order of proximity to the probe 11, and the first rate of transmission and reception is completed at the time when the first echo 31 is expected to return from the deepest part of the imaging region. The first echo 31 is transmitted as the first received signal 32 to the signal processor 27 through the transmit/receive switch 21, the receive amplifier 24, A/D converter 25 and the receive beamformer 26.

After the first rate of transmission and reception is completed, the transmit amplifier 22 and the probe 11 are electrically re-connected by the transmit/receive switch 21. Next, an another transmit pulse waveform is formed at the pulse synchronizer 23, and transmitted via the transmit amplifier 22 and the transmit/receive switch 21 to the probe 11, from which the second fundamental wave pulse 33 is irradiated onto the subject. The second fundamental pulse 33 has the waveform, which is roughly plus-minus inverted waveform of the first fundamental wave pulse 30. Moreover, it is desirable that the pulse synchronizer 23 has such means to remove electrical distortion generated at the transmit amplifier 22 and the effect of phase rotation attributable to the frequency characteristic of the probe 11, and to adjust the waveform of at least the first fundamental wave pulse 30 or the second fundamental wave pulse 33.

The second fundamental wave pulse 33 propagates in the subject body while generating waveform distortions due to acoustic nonlinear effects and repeating reflections and penetrations in a boundary of different acoustic impedance. After the second fundamental wave pulse 33 is irradiated from the probe 11, the transmit/receive switch 21 electrically connects the receive amplifier 24 and the probe 11 immediately according to the instructions from the controller 29. The echo reflected from the subject sequentially arrives at the probe 11, as the second received echo 34, in the order of proximity to the probe 11, and the second rate of transmission and reception is completed at the time when the second echo 34 is expected to return from the deepest part of imaging region. The second received echo 34 is transmitted as the second received signal 35 to the signal processor 27 through the transmit/receive switch 21, the receive amplifier 24, the ND converter 25 and the receive beamformer 26.

FIG. 2 shows an example of detailed configuration of the signal processor 27 shown in FIG. 1. The signal processor 27 has temporary memories 40 and 41, an adder 42, a quadrature detecting processor 43 and a filtering processor 44. The output from the filtering processor 44 is further processed in a B-mode processor 45 and a Doppler processor 46 and outputted in the imaging processor 28. In the temporary memories 40 and 41 the first received signal 32 of the first rate and the second received signal 35 of the second rate are temporarily stored respectively and added then at the adder 42.

The received signals added here contain received signal components made of fundamental wave components constituting the first fundamental wave pulse 30 and the second fundamental wave pulse 33, and the received signal components made of nonlinear components generated based on the nonlinear propagation of these fundamental wave pulses in the subject body. However, since the phase of the fundamental wave components of the first fundamental wave pulse 30 is inverted by 180 degree from that of the second fundamental wave pulse 33, sum of them is ideally zero.

On the other hand, as the nonlinear components are generated as a result of the square of the fundamental wave component, there is no phase inversion, and the signal to noise ratio (S/N) can be improved by about 3 dB by addition. By this, only nonlinear components can be extracted by this adding process. It can also be configured that the ratio of strength between the first received signal 32 and the second received signal 35 can be changed continuously in the time direction (depth direction for the imaging region) automatically or manually. And it is also possible to configure to allow users to adjust aforementioned ratio through the outer interface 12.

The quadrature detecting processor 43 applies frequency shift depending on the reference frequency and provide in-phase signal components and quadrature signal components. Extracted nonlinear components are high-frequency and low-frequency harmonic components, which are generated in the receiving band of the probe 11. Since the higher frequency components undergo stronger frequency-dependent attenuation, the received signals from the point deeper than the transmission focal point are composed mostly of low frequency components. Accordingly, it is desirable to select, as a reference frequency at the quadrature detecting processor 43, higher frequency for the signals received from relatively shallow region up to the transmission focal point, and lower frequency for the received signals from the depth. As a result it is possible to configure to be able to change the reference frequency continuously in the time direction (depth direction for the imaging region) automatically or manually. And it can be also configured to allow users to adjust the reference frequency through the outer interface 12.

The signal components in the frequency band to be used as image data are extracted at the filtering processor 44 from the signals after the quadrature detection and used to construct the data for B-mode images for displaying the strength of reflected echo as brightness information and the data such as blood flow rate to be calculated based on the Doppler effect at the B-mode processor 45 and the Doppler processor 46. The imaging processor 28 converts these data into space data by appropriate coordinate conversion and delivers them to the display 13. With this, the display 13 displays B mode images and the blood flow data and others as image.

Next, the fundamental wave component of the transmission pulse in this embodiment will be explained in detail.

According to this embodiment, a single pulse wave having a single frequency peak as shown in FIG. 3 is used as a fundamental wave component 71 of the first fundamental wave pulse 30 and the second fundamental wave pulse 33. The fundamental wave component 71 has the peak frequency of $f_c$ and the bandwidth of $2f_s$. Accordingly, the band of the fundamental wave component is from $f_c-f_s$ to $f_c+f_s$. Unless these frequencies $f_c$ and $f_s$ are set appropriately as shown in FIG. 3, many of the low-frequency harmonic components 72 and high-frequency harmonic components 73 are generated outside the probe-sensitive band 74 and cannot be detected. In this embodiment, however, the frequencies $f_c$ and $f_s$ are set at given values relative to the probe-sensitive band from $f_1$ to $f_2$ as shown in FIG. 4. Accordingly, many of the low-frequency harmonic components 72 and high-frequency harmonic components 73 can be generated within the probe-sensitive band $f_1-f_2$ as shown in FIG. 4. The lower limit frequency $f_1$ in the probe-sensitive band is not defined by the bandwidth of −6 dB which is generally used, but is the lower limit frequency of the signal components which can be used as image signals in the received echo signal component after passing through the probe.

Firstly, the relationship between the nonlinear components used for imaging and the fundamental frequency components, which the first fundamental pulse and the second fundamental pulse have, will be explained by using formulas and diagrams.

Nonlinear imaging of the present invention effectively captures nonlinear components derived from the fundamental frequency component due to acoustic nonlinear effects in the subject body and achieves both higher resolution and improved ultrasound penetration. The way of propagation of sound wave is expressed mathematically by the Khokhlov- Zabolotskaya-Kuznetsov equation (KZK equation) or the Burgers' equation shown in Formula 1.

$$\frac{\partial p}{\partial x} - \frac{b}{2\rho c^3}\frac{\partial^2 p}{\partial t^2} = \frac{\beta}{2\rho c^3}\frac{\partial p^2}{\partial t} \quad [\text{Formula 1}]$$

Formula 1 describes nonlinear acoustic propagation in the direction of x in 1-D space, where p is sound pressure, $\rho$ is density, c is speed of sound, $\beta$ is nonlinear coefficient and t is delay time in the coordinate system which moves at the speed of sound c in the direction of x. b is the amount of substance associated with the absorption of sound wave, and its relationship with the absorption coefficient $\alpha$ and the angular frequency $\omega$ is expressed by the equation, $\alpha=\omega w^2$. The right side member of Formula 1 expresses the term of virtual source which arises in the course of nonlinear propagation. If third or higher harmonics is neglected, and the changes in waveform in the direction of x are not remarkable with least attenuation per wavelength, the nonlinear components to be generated can be estimated by temporal differentiation of the square value of linear sound pressure. Considering the fundamental wave obtained by subjecting the carrier frequency $f_c=\omega_c/2\pi$ to amplitude modulation with the modulating frequency $f_s=\omega_s/2\pi$ and the degree of modulation m, the band of the nonlinear components to be generated, their phase and amplitude will be explained below.

Here, the amplitude modulated wave $p(t)=p_0(1+m \cos 2\pi f_s t)\cos 2\pi f_c t$ is used as the fundamental wave, for example. The results of calculation using nonlinear components generated by the acoustic nonlinear effects as $dp^2/dt$ are expressed by Formula 2.

$$\frac{dp^2}{dt} = \frac{d}{dt}\{p_0(1+m\cos\omega_s t)\cos\omega_c t\}^2 =$$
$$\frac{p_0^2}{2}(-2m\omega_s\sin\omega_s t - m^2\omega_s\sin 2\omega_s t)(1+\cos 2\omega_c t) -$$
$$p_0^2\omega_c\left\{1 + 2m\cos\omega_s t + \frac{1}{2}(1+\cos 2\omega_s t)\right\}\sin 2\omega_c t =$$
$$-2m\pi f_s p_0^2 \sin 2\pi f_s t - m^2\pi f_s p_0^2 \sin 4\pi f_s t -$$
$$\frac{m^2\pi}{2}(f_c - f_s)p_0^2\sin 2\pi(2f_c - 2f_s)t -$$
$$m\pi(2f_c - f_s)p_0^2\sin 2\pi(2f_c - f_s)t - (2+m^2)\pi f_c p_0^2$$
$$\sin 4\pi f_c t - m\pi(2f_c + f_s)p_0^2\sin 2\pi(2f_c + f_s)t -$$
$$\frac{m^2\pi}{2}(f_c + f_s)p_0^2\sin 2\pi(2f_c + 2f_s)t$$

[Formula 2]

This result suggests that seven frequency components are generated as nonlinear components, such as $f_s$, $2f_s$, $2f_c-2f_s$, $2f_c-f_s$, $2f_c$, $2f_c+f_s$ and $2f_c+2f_s$, all of which are components in-phase.

These seven nonlinear components are generated when the fundamental wave is continuous wave. In this embodiment, since the fundamental wave is a single pulse wave, these seven components will have a number of bands around the frequency component of seven nonlinear components as shown in FIGS. 5 (a) and (b). FIGS. 5 (a) to (c) shows the amplitude spectrum of nonlinear component where the degree of modulation m is set as 1, the carrier frequency $f_c$ as 2.5 MHz and the modulating frequency $f_s$ as 0.5 MHz and when the pulse width is changed to $9/f_s$, $3/f_s$ and $1/f_s$.

As known from FIG. 5 (a) to (c), when the pulse width becomes shorter, the aforementioned seven frequency components are roughly divided into two bands, the low-frequency harmonic component 72 consisting mainly of $f_s$ and $2f_s$, and the high-frequency harmonic components 73, consisting mainly of the band ranging from $2f_c-2f_s$ to $2f_c+2f_s$ with $2f_c$ as a center.

In the conventional THI or nonlinear imaging using low-frequency harmonic components, because of the absence of the probe band that can detect both low-frequency harmonic components 72 and high-frequency harmonic components 73 as shown in FIG. 5(c), only one of the components could be extracted. However, as mentioned earlier, when the high-frequency harmonic component (second harmonic component) is used in THI (see FIG. 17), the penetration in deeper region may become insufficient. Also, when the low-frequency harmonic component surrounding DC or the difference-frequency wave component is used (see FIG. 19), only a trace amount of converted energy out of the nonlinear component energy-converted from the fundamental frequency components can be used, and a problem that sufficient S/N and dynamic range cannot be ensured. Moreover, in some probe-sensitive band, the energy-use efficiency is further decreased.

The concept of the present invention is to generate nonlinear components, which will be produced from the fundamental frequency component by energy conversion, within the probe-sensitive band as far as possible. This may maximize the energy-use efficiency and achieve higher resolution as well as better ultrasound penetration in deep.

As shown in FIG. 5 (a) to (c), nonlinear components, which are generated by irradiating fundamental frequency pulse 71 with a certain band, are divided into low-frequency harmonic component 72 and high-frequency harmonic component 73, depending on the said band. The received echo as a whole is a reflected echo within the band containing the fundamental frequency component 71 and the nonlinear components 72 and 73 as shown in FIG. 3, and nonlinear components 72 and 73 are generated in the frequency band distant from the fundamental frequency component 71. In this invention, appropriate setting the frequency $f_c$ and the band $2f_s$ of the fundamental frequency component 71 makes it possible to bring the band, in which the nonlinear components 72 and 73 are generated, closer to the fundamental frequency component 71 and to superimpose it on the fundamental frequency component 71, and contain many bands of the nonlinear components 72 and 73 in the probe-sensitive band 74. The fundamental frequency component 71, even if it is superimposed on the nonlinear components 72 and 73, can be removed by using pulse inversion method.

Conditions for setting the fundamental frequency component 71 to enable the band of the nonlinear components consisting of low-frequency harmonic component 72 and the high-frequency harmonic component 73 to superimpose on the probe-sensitive band ranging from $f_1$ to $f_2$ will be explained in detail.

The probe-sensitive band 74 for both transmission frequency band and received frequency band is set as ranging from $f_1$ to $f_2$ ($f_1<f_2$). The fundamental frequency component 71 is the amplitude modulating wave with the carrier frequency of $f_c$ and the modulating frequency of $f_s$ as mentioned above. The frequency band of the fundamental frequency component 71 is from $f_c-f_s$ to $f_c+f_s$. So for this component to be included in the probe-sensitive band, the conditions of $f_c-f_s \geq f_1$ and $f_c+f_s \leq f_2$ must be satisfied.

As is known from Formula 2, there are two possible cases. The lowest frequency component of all generated nonlinear components is $f_s$ in one case and $2f_c-2f_s$ in other case. The conditions required for containing either of these components in the probe-sensitive band 74 is $f_s \geq f_1$ for the former and $2f_c-2f_s \geq f_1$ for the latter.

If the lowest frequency of the nonlinear component is $f_s$, it should satisfy $f_s \geq f_1$ to be contained in the probe-sensitive band 74. As the condition, $f_c-f_s \geq f_1$, to contain the lower limit frequency of the fundamental frequency 71 in the probe-sensitive band 74 must be also satisfied, the conditions should be $f_s \geq f_1$ and $f_c \geq 2f_s$. Namely, in this embodiment, the modulation frequency $f_s$ of the amplitude modulation wave is set higher than the lower limit frequency $f_1$ of the probe-sensitive band 74, while the carrier frequency $f_c$ is set as twice or more of the modulation frequency $f_s$.

Further, the condition, $2f_c+2f_s \leq f_2$, for the highest frequency component, $2f_c+2f_s$ (high-frequency harmonic component) of all generated nonlinear components to be contained in the probe-sensitive band 74, and the condition, $f_c+f_s \leq f_2$, for the upper limit frequency of the fundamental frequency component 71 to be contained in the probe-sensitive band 74, should also be satisfied. In addition, the conditions to contain the lower limit frequency $f_1$ in the probe-sensitive band 74, $f_s \geq f_1$ and $f_c \geq 2f_s$ should also be satisfied. It is known from these, that the upper limit frequency $f_2$ of the probe-sensitive band 74 should satisfy $f_2 \geq 6f_1$.

However, as the fractional bandwidth of the probe 11 made of piezoelectric material such as PZT is about 80% at maximum, it is difficult to achieve the probe 11 having a wide probe-sensitive band 74 of namely ranging from $f_1$ to $6f_1$ (fractional bandwidth is 143%) at present. On the other hand, as it is clear from Formula 2, since the high-frequency harmonic component 73, of the generated nonlinear components, contains more energy than the low-frequency harmonic component 72, the level of detection (energy to be detected) of the high-frequency harmonics component 73 in the high frequency band by the probe 11 is higher than the level of the low-frequency harmonic component 72 in the low frequency band. In this embodiment, therefore, with priority to improving the detection level of the low-frequency harmonic component 72 in the low frequency band, which may seriously affect in-depth penetration, all bands of the low-frequency harmonic component 72 are made to be contained in the probe-sensitive band 74, and the maximum possible bands of the high-frequency harmonic component 73 are made to be contained in the probe-sensitive band 74, as shown in FIG. 4.

Particularly, by setting the lower limit frequency of the low-frequency harmonic component 72 as identical with the lower limit frequency for the probe-sensitive band as shown in FIG. 4, the whole band of the low-frequency harmonic component 72 is made to be contained in the probe-sensitive band 74 and the band of the high-frequency harmonic component 73 to be contained in the probe-sensitive band 74 is maximized. In other words, if the lowest frequency component of the generated nonlinear components is $f_s$, based on the conditions of $f_s \geq f_1$ and $f_c \geq 2f_s$, the modulating frequency $f_s$ is set as the lower limit frequency $f_1$ in the probe-sensitive band 74 ($f_s = f_1$) and the amplitude modulation frequency $f_c$ is set as twice of the modulating frequency $f_s$ ($f_c = 2f_s$).

Even under these conditions, the high-frequency harmonic component 73 on the higher frequency side can be caught by expanding fractional bandwidth of the probe sensitivity through the adjustment of the matching layer of the probe 11 and the use of single crystal piezoelectric element and capacitive micro-machined ultrasound transducer.

If the probe 11 having a wide sensitive band from $f_1$ to $6f_1$ can be achieved, $f_c$ and $f_s$ are set to satisfy $2f_c+2f_s \leq f_2$ and $f_c+f_s \leq f_2$, the conditions for the highest frequency components of the generated nonlinear components, $2f_c+2f_s$(high-frequency harmonic component) to be contained in the probe-sensitive band 74. By this, all nonlinear components can be generated in the probe-sensitive band 74 of the probe 11 and caught.

Then, for the case in which the lowest frequency of nonlinear components is $2f_c-2f_s$, the condition required for the frequency to be higher than the lower limit frequency, $f_1$, of the probe 11 is $2f_c-2f_s \geq f_1$. In this case, since the frequency $f_s$ which arises as the low-frequency harmonic component 72 of the nonlinear components satisfies the condition, $f_s \geq f_1$, the $2f_c-2f_s \geq f_s$ is also satisfied and therefore $f_c \geq 1.5f_s$. The condition, $f_s \geq 2f_1$, is obtained by using the condition of the lower limit frequency of the fundamental frequency components 71, $f_c-f_s \geq f_1$. However, in order to satisfy the condition, $2f_c+2f_s \leq f_2$, for the upper limit frequency of the high-frequency harmonic component to be contained in the probe-sensitive band 74, there must be $f_2 \geq 10f_1$. It therefore requires further wider probe-sensitive band 74 than the aforementioned case of $f_s \geq f_1$, it becomes more unlikely to be realized.

Based on all stated above, in this embodiment, if the aforementioned amplitude modulation wave is the fundamental frequency component 71 as mentioned above, the modulating frequency $f_s$ is set as the lower limit frequency in the probe-sensitive band, $f_1$ ($f_s = f_1$), and the carrier frequency $f_c$ as twice higher than the modulating frequency ($f_c = 2f_s$). Furthermore, by taking into account that the frequency band of this amplitude modulation wave ranges from $f_c-f_s$ to $f_c+f_s$, it can be described more generally that, when the lower limit frequency in the probe-sensitive band is $f_1$, the frequency band of the fundamental frequency component 71 is set as from $f_1$ to $3f_1$.

This condition of the fundamental frequency component 71 is applied when the transmit/receive sensitivity band of the probe 11 is the same. For example, when some of the arrays constituting the probe 11 are used exclusively for transmission, the transmission frequency band of the array exclusively for transmission and the reception frequency band of the reception array can be selected based on the concept of the present invention to improve energy-use efficiency of nonlinear components. Even in this case, it is desirable to set that the lowest frequency component among arising low-frequency harmonic component can be caught by the receiving array.

The setting of the band of the fundamental frequency component 71 has been above explained. The waveform of the fundamental wave irradiated in the subject body in nonlinear imaging using the ultrasound diagnostic equipment of this invention will be explained below.

Nonlinear components expressed by Formula 2 use the amplitude modulating wave $p(t)=p_0(1+m \cos 2\pi f_s t) \cos 2\pi T_c t$ as fundamental wave. Similar calculation is performed for the carrier wave component $f_c$ and the modulating wave component $f_s$, in both sine and cosine wave cases. The phase at $t=0$ of the aforementioned seven nonlinear components in both cases are summarized in FIG. 6.

It is understood from FIG. 6 that all nonlinear components are in-phase when the carrier wave component $f_c$ and the modulating wave component $f_s$ are cosine wave. Since the amplitude of sound pressure of nonlinear components to be detected is the sum of the amplitudes of seven nonlinear component waveforms, if all nonlinear components are in-phase, the maximum amplitude of sound pressure to be detected is the sum of the amplitudes of these seven nonlinear components. Consequently, it is possible to detect large amplitude and achieve good image quality of high resolution.

Thus, in order to obtain signals of wide band nonlinear components for achieving high quality images, it is desirable that both carrier wave component and modulating wave component are expressed by cosine wave as $p(t)=p_0(1+m \cos 2\pi f_s t) \cos 2\pi f_c t$. This is applicable to the Fourier expansion of fundamental wave, in which all frequency components are expressed only by cosine wave, and high-resolution nonlinear imaging is achieved by transmitting the pulse wave having such fundamental frequency component.

Meanwhile, the nonlinear components which arise by the fundamental wave consisting only of spectral components of sine wave, as $p(t)=p_0(1+m \cos 2\pi f_s t) \sin 2\pi f_c t$, are in-phase for each of low-frequency harmonic component 72 and high-frequency harmonics component 73. For the imaging in a living body, there is a mechanical index (MI), specified for each site of imaging is applied for the safety consideration, and particularly the limit on the amplitude of sound pressure at the negative pressure side. As aforementioned, when all Fourier series components of the fundamental wave are given by cosine wave, the maximum amplitude of sound pressure is expressed as a sum of the amplitudes of all frequency components. When all Fourier series components of the fundamental wave are given by sine wave, the maximum amplitude of sound pressure becomes less than the sum of the amplitudes of all frequency components. For example, the maximum amplitude of $\cos \omega t + \cos 2\omega t$ is 2, whereas the maximum amplitude of $\sin \omega t + \sin 2\omega t$ is $\sqrt{3}$. This means that under the conditions where MI is constant, the fundamental wave whose Fourier series components are all sine wave components can be set to have larger pulse power (amplitude of sound pressure) than the fundamental wave whose Fourier series components are all cosine components.

As it is apparent from Formula 2, nonlinear components which arise with the propagation of sound wave due to acoustic nonlinear effects are proportionate to the square of the sound pressure amplitude. Therefore, when the fundamental wave whose Fourier series components are all sine components is transmitted, higher levels of low-frequency harmonics and high-frequency harmonics are obtained than when the fundamental wave whose Fourier series components are all cosine wave components is transmitted. Accordingly, in order to give priority to improving the ultrasound penetration in the deep part of the imaging region than to improving resolution, it is desirable to transmit the fundamental wave whose Fourier series components consist only of sine components.

Therefore, it is desirable to configure that the setting of the waveform can be changed automatically or manually, so that the users who want to give priority to improving resolution can set both carrier wave component $f_c$ and modulating wave component $f_s$ as cosine wave, whereas those who want to give priority to improving the ultrasound penetration can set both carrier wave component $f_c$ and modulating wave component $f_s$ as sine wave.

In order to confirm the propagation characteristic of the transmission waveform when the waveform of the fundamental wave is cosine or sine wave as mentioned above, the propagation characteristics of the transmission waveform was obtained by the analysis of nonlinear propagation of sound wave by using the KZK equation. The result of the analysis is explained below. The propagation characteristics which are identical with the results of the pulse inversion are also obtained. Here, all analyses shown below were conducted by assuming a uniform acoustic medium which is similar to the physical property of living body, and using the speed of sound of 1500 m/s, density of 1000 kg/m$^3$, nonlinear parameter B/A of 7 and frequency-dependent absorption coefficient of 0.7 dB/cm/MHz. The calculation for 2-D sound field model assumed 1-D array with an aperture of 40 mm and the distance of 100 mm from the array front as a focal point. Furthermore, the transmission- and reception-sensitive band of the probe 11 was set as the range from about 1 MHz to 5 MHz, and the maximum sound pressure amplitude of the fundamental wave pulse on the probe surface as 4 MPa (rms). (Fundamental Waveform in which Fourier Series Components are Given Only by Cosine Waves)

In order to generate wide-band and large-amplitude nonlinear components for achieving higher resolution, it is desirable that the Fourier series components consist of only cosine components as mentioned above. The amplitude modulating wave, $p(t)=p_0(1+\cos 2\pi f_s t) \cos 2\pi f_c t$ with the degree of modulation m=1, was used as the fundamental wave. And based on the aforementioned conditions for setting the fundamental frequency component 71, the modulating frequency $f_s$ is set as the lower limit frequency in the transmit/receive band of the probe, 1 MHz, and the carrier frequency $f_c$ as twice of $f_s$, 2 MHz. Moreover, as it is apparent from FIGS. 5(a), (b) and (c), a shorter pulse width of the fundamental wave to be transmitted is better for widening the band of the nonlinear components. In this embodiment, therefore, the pulse width was set as $1/f_s$, one wavelength of the modulating frequency $f_s$. The band of the fundamental pulse to be transmitted of −6 dB ranges from 1 MHz to 3 MHz, and falls in the assumed probe-sensitive band.

FIG. 7 is the results of analysis showing the changes in waveform of the aforementioned fundamental wave pulse 30 along the sound axis, where the waveform corresponds to that of the first received echo 31 from each position on the sound axis. The horizontal axis expresses delay time in movement with speed of sound in the direction of sound axis. FIG. 8 shows the results of similar analysis showing the changes in waveform of the second fundamental wave pulse 33, which is the fundamental pulse in FIG. 7 with positive/negative inversion and corresponds to the waveform of the second received echo 34. In FIG. 7 and FIG. 8, (a) is the surface of the probe 11, (b) is the distance of 10 mm on the sound axis, (c) and (d) are waveforms at the distance of 100 mm and 200 mm, respectively. The fundamental waveform given by Fourier series components consisting only of cosine wave is, as apparent in FIG. 7(a) and FIG. 8(a), symmetric about the time center of the fundamental wave pulse. Such the waveform is given by the inverse Fourier transformation of, for example, cosine roll off function. In this case, cut-off frequency has just to be set to have the band from $f_1$ to $3f_1$, where $f_1$ is the lower unit frequency of the probe-sensitive band 74.

As it is understood from FIG. 7 and FIG. 8, propagating sound wave is subject to the distortion of waveform due to acoustic nonlinear effects and frequency-dependent attenuation. Namely, the waveform distortion means the generation of nonlinear components, while the frequency-dependent attenuation means that because the components at the higher frequency side attenuate more, only the signal components of narrow band at the lower frequency side remain in deep region.

FIG. 9 (a)-(d) shows the sum of the waveforms at different distances in (a)-(d) in FIGS. 7 and 8. Addition of the results of (a)-(d) in FIGS. 7 and 8 gives the waveform identical to that obtained by pulse inversion. As the linear components of the first and second fundamental wave pulse, 30 and 33 respectively, are removed by the addition, the waveforms shown in FIG. 9 (a)-(d) consist only of the nonlinear components.

FIG. 10 is an amplitude spectrum of waveform consisting of nonlinear components as shown in FIG. 9 (b)-(d). FIG. 11 is a distant characteristics diagram showing the maximum sound pressure amplitude of the waveform after pulse inversion relative to distance on the sound axis. It is apparent from FIG. 10 that at the distance of 10 mm on the sound axis non linear components are generated intensively in the range from 1 MHz to 5 MHz, which is assumed as the probe-sensitive band. This indicates that the energy of nonlinear components can be very efficiently used for imaging. As it is also apparent from FIG. 11, nonlinear components of such wide band are effective up to the focal distance of 100 mm, but attenuate dramatically after the focal distance. As known from the amplitude spectrum at the distance of 200 mm along the sound axis, only narrow-band signal components at the lower frequency side remain in such range. Therefore, in such range, the linear components may be used for imaging by changing the ratio of addition of the first and second received echoes 31 and 34.

Nonlinear components are generated prominently in the high-frequency harmonic component 74 of the fundamental wave pulse, but they undergo attenuation in the course of propagation and the low-frequency harmonic components 72 remain in the deep region. Since the optimal frequency band usable for imaging changes with the distance of propagation, it is desirable to change the reference frequency in the direction of distance in the quadrature detection after pulse inversion. Namely, if this analysis is used as an example, it is necessary only to continuously change the reference frequency from 5 MHz to 4 MHz in the distance of up to 100 mm, 3 MHz at 150 mm and 2 MHz from 180 mm or more from the focal point.

(Fundamental Waveform where all Fourier Series Components are Given with Sine Wave)

In order to generate high-energy nonlinear components while giving priority to improving ultrasound penetration, it is desirable as mentioned above that the Fourier series components consist only of sine waves. Therefore, the amplitude modulating wave, $p(t) = p_0(1 + \cos 2\pi f_s t) \sin 2\pi f_c t$ with the degree of modulation m=1, was used as the fundamental wave. And based on the aforementioned conditions of the fundamental wave, the modulating frequency $f_s$ is set as 1 MHz, a lower limit frequency in the probe's transmission-reception band, while the carrier wave frequency $f_c$ is set as 2 MHz, twice of $f_s$. Since the nonlinear components are generated by nonlinear interaction in the region where the fundamental frequency pulse is present, the resolution can be improved by shortening the pulse width. Accordingly, one wavelength of the modulating frequency $f_s$ was set as the pulse length in this case. The band of fundamental wave pulse to be transmitted at −6 dB is from 1 MHz to 3 MHz, and is contained in the assumed probe-sensitive band 74.

FIG. 12 is the results of analysis showing the changes in waveform along the sound axis of the aforementioned fundamental wave pulse 30, where the waveform corresponds to that of the first received echo 31 from each position on the sound axis. The horizontal axis expresses delay time in movement with speed of sound in the direction of sound axis. FIG. 13 shows the results of similar analysis showing the changes in waveform of the second fundamental wave pulse 33, which is the fundamental pulse in FIG. 12 with positive/negative inversion and corresponds to the waveform of the second received echo 34. In FIG. 12 and FIG. 13, (a) is the surface of the probe 11, (b) is the distance of 10 mm on the sound axis, (c) and (d) are the waveforms at the distance of 100 mm and 200 mm, respectively.

As it is known from FIG. 12 and FIG. 13, the sound wave is subject to the distortion of waveform in the course of propagation due to acoustic nonlinear effects and frequency-dependent attenuation. Namely, the waveform distortion means the generation of nonlinear components, while the frequency-dependent attenuation means that because the components at the higher frequency side attenuate more, only the signal components of narrow band at the lower frequency side remain in deep region.

FIG. 14 (a)-(d) each shows the sum of the waveforms at different distances shown in (a)-(d) in FIGS. 12 and 13. Addition of the results in (a) to (d) in FIGS. 12 and 13 gives the waveform identical to that obtained by pulse inversion. As the linear components of the first fundamental pulse 30 and the second fundamental pulse 33 are removed by the addition, the waveforms shown in FIG. 14 consist only of the nonlinear components.

FIG. 15 is an amplitude spectrum of the waveform consisting of nonlinear components shown in FIG. 14 (b)-(d), and FIG. 16 is a distant characteristics diagram showing the maximum sound pressure amplitude of the waveform after pulse inversion relative to the distance on the sound axis. As known from the results of analysis at the distance of 10 mm on the sound axis in FIG. 15, because the fundamental wave pulse consisting only of sine wave components has an inverted phase between high- and low-frequency harmonic components, the notch will appear in the amplitude spectrum. However, as it is apparent from the comparison between the results of FIG. 10 and FIG. 15, under the condition in which the maximum sound pressure amplitude of the fundamental wave pulse is fixed constant, the fundamental wave pulse consisting only of sine wave components can increase the energy of the original pulse than the fundamental wave pulse consisting only of cosine components can do. As a result, the efficiency of energy conversion from fundamental wave components to nonlinear components can be increased. Comparison between FIG. 11 and FIG. 16 also suggests that when the fundamental wave pulse is constituted only by sine wave components the energy is higher by about 3 dB even at the position 150 mm beyond the focal point.

As it is known from FIG. 16, on the other hand, such nonlinear components are effective up to the focal distance of about 100 mm, but dramatically attenuate beyond this point. As it is apparent from the amplitude spectrum at the distance of 200 mm on the sound axis in FIG. 15, because only narrow band signal components at the lower frequency side remain in this region, the linear components can be used for imaging by changing the ratio of addition of the first and second received echo 31 and 34 in this region.

Also, of the nonlinear components the high-frequency harmonic component 73 of the fundamental wave pulse are generated prominently, but they undergo attenuation in the course of propagation and the low-frequency harmonic components 72 remain in the deep region. Accordingly, since the optimal frequency band usable in imaging changes with propagation distance, it is desirable to change the reference frequency in the direction of distance in the quadrature detection after pulse inversion. Namely, if this analysis is used as an example, it is necessary only to continuously change the reference frequency from 5 MHz to 4 MHz in the distance of up to 100 mm, 3 MHz at 150 mm and 2 MHz from 180 mm or more from the focal point.

The ultrasound diagnostic equipment 10 of the present invention may be equipped with additional functions with which optimal choice of the waveform of fundamental wave (sine or cosine) as abovementioned can be automatically adjusted by the controller 29 depending on the depth of imaging region, or configured to allow users to select the waveform freely from the outer interface 12. When the waveforms of the first and second fundamental wave pulse are transmitted as an amplitude modulating wave as mentioned above, the controller 29 or the pulse synchronizer 23 may be equipped with the functions which allow users to adjust the bands of fundamental wave pulse 30 and 33 by increasing or decreasing the modulating frequency $f_s$ through the outer interface 12. By equipping these adjusting functions, the image quality with optimal resolution, brightness and uniformity of image can be obtained.

In the aforementioned embodiment the amplitude modulating wave is used as the first and second fundamental wave pulse to be transmitted. As a fundamental wave pulse having similar frequency band with it, the waveform whose frequency varies in the direction of sound axis can be used. The first fundamental wave pulse whose frequency varies decreasingly (increasingly) and the second fundamental wave pulse whose frequency varies increasingly (decreasingly) may also be used.

Here, the waveform with changing frequency may be a cycle or combined cycles of the waveform with different frequency, for example. It can be configured to combine fractions such as ½ cycle, ¼ cycle and ⅛ cycle of the waveform with different frequency, for example. A chirp waveform whose frequency changes continuously may be also used.

As stated above, since the ultrasound diagnostic equipment of the present invention, in ultrasound nonlinear imaging, can contain many of the nonlinear components generated by the nonlinear interaction of ultrasound in the subject body in the probe-sensitive band 74 by setting the band of the fundamental wave component 71 of the transmission pulse in relation to the probe-sensitive band 74, the nonlinear components can be caught highly efficiently by the probe 11. This achieves higher resolution and improves ultrasound penetration deep in the imaging region at the same time, thereby creating a uniform and high-quality image over the entire imaging region.

Appropriate selection of the fundamental waveform (cosine or sine wave) of transmission pulse according to the depth of the imaging region can provide the images with excellent resolution, brightness and uniformity.

DESCRIPTION OF NOTATIONS

Figure 1:
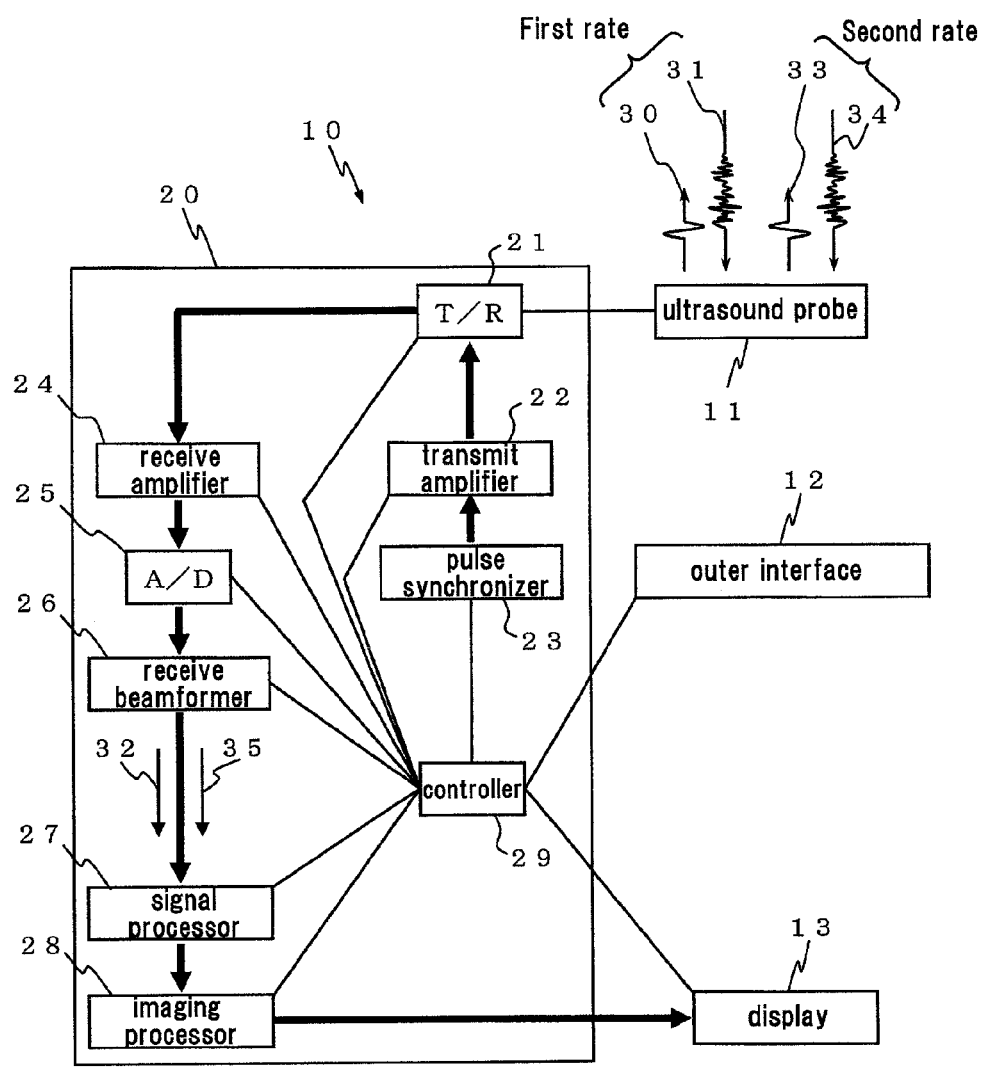
FIG. 1
A block diagram showing the configuration of the ultrasound diagnostic equipment of one embodiment of the present invention FIG. 2
A block diagram showing the configuration of one embodiment of the signal processor contained in the ultrasound diagnostic equipment of the present invention FIG. 3
A spectrum showing the frequency and the amplitude of the fundamental frequency component and the nonlinear component contained in the echo reflected from the subject FIG. 4
A spectrum showing the frequency and the amplitude of the fundamental frequency component and the nonlinear components generated according to the embodiment of the present invention FIG. 5(a)-(c)
An amplitude spectrum of the nonlinear component generated with the amplitude modulating wave as the fundamental wave in the embodiment of the present invention FIG. 6
A diagram explaining the phase relation of nonlinear components generated with the amplitude modulating wave as the fundamental wave in the embodiment of the present invention FIG. 7(a)-(d)
Graphs showing the nonlinear propagation waveform of the first fundamental wave pulse 30 consisting of cosine components in the embodiment of the present invention FIG. 8(a)-(d)
Graphs showing the nonlinear propagation waveform of the second fundamental wave pulse 33 consisting of cosine components in the embodiment of the present invention FIG. 9(a)-(d)
Graphs showing the waveform after pulse inversion by the fundamental wave pulse consisting of cosine components in the embodiment of the present invention FIG. 10
A graph showing the amplitude and the frequency of waveform after pulse inversion by the fundamental wave pulse consisting of cosine components in the embodiment of the present invention FIG. 11
A graph showing distant characteristics on the sound axis for the maximum sound pressure amplitude of the waveform after pulse inversion by the fundamental wave pulse consisting of cosine components in the embodiment of the present invention FIG. 12(a)-(d)
Graphs showing the nonlinear propagation waveform of the first fundamental pulse consisting of sine components in the embodiment of the present invention FIG. 13(a)-(d)
Graphs showing the nonlinear propagation waveform of the second fundamental pulse consisting of sine components in the embodiment of the present invention FIG. 14(a)-(d)
Graphs showing the waveforms after pulse inversion by the fundamental wave pulse consisting of sine components in the embodiment of the present invention FIG. 15
A graph showing the amplitude and the frequency of waveform after pulse inversion by the fundamental wave pulse consisting of sine components in the embodiment of the present invention FIG. 16
A graph showing distance characteristics on the sound axis of the maximum sound pressure amplitude of the waveform after pulse inversion by the fundamental wave pulse consisting of sine components in the embodiment of the present invention FIG. 17
A diagram explaining the conventional harmonic imaging method in the frequency domain FIG. 18
Diagrams explaining the method of pulse inversion FIG. 19
A diagram explaining the conventional nonlinear imaging method using low-frequency harmonics in the frequency domain
Figure 2:
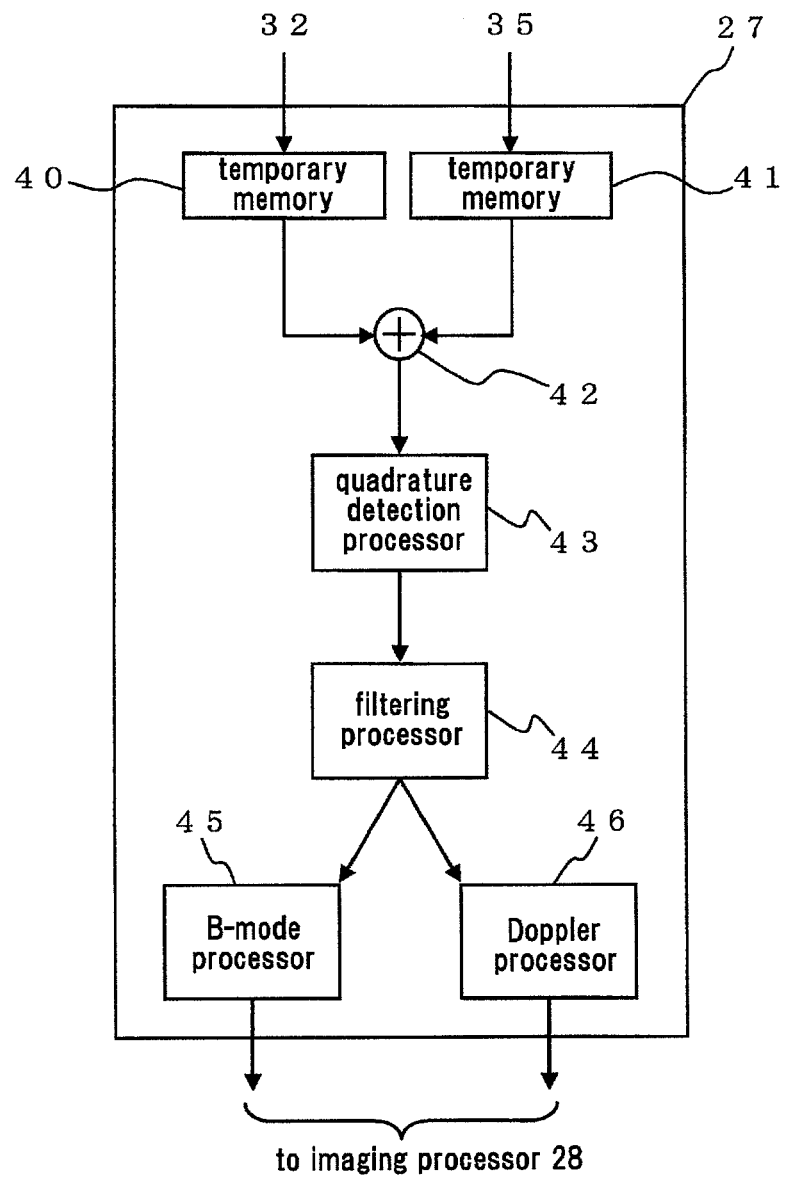
Figure 3:
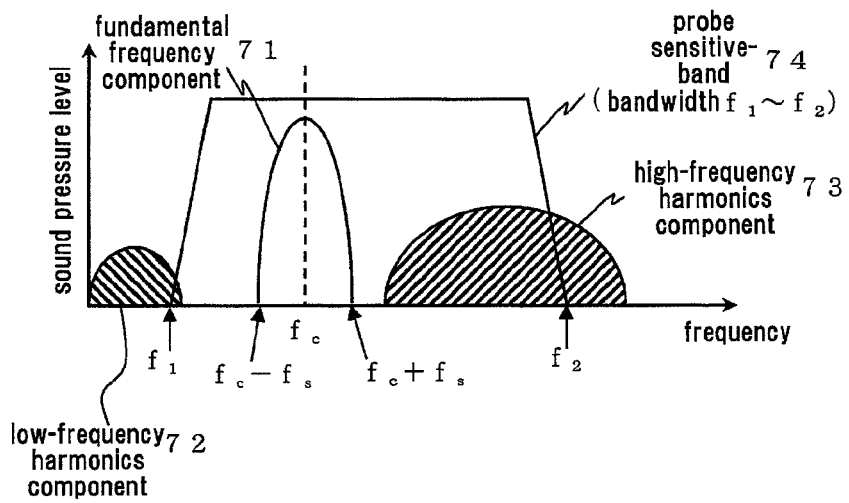
Figure 4:
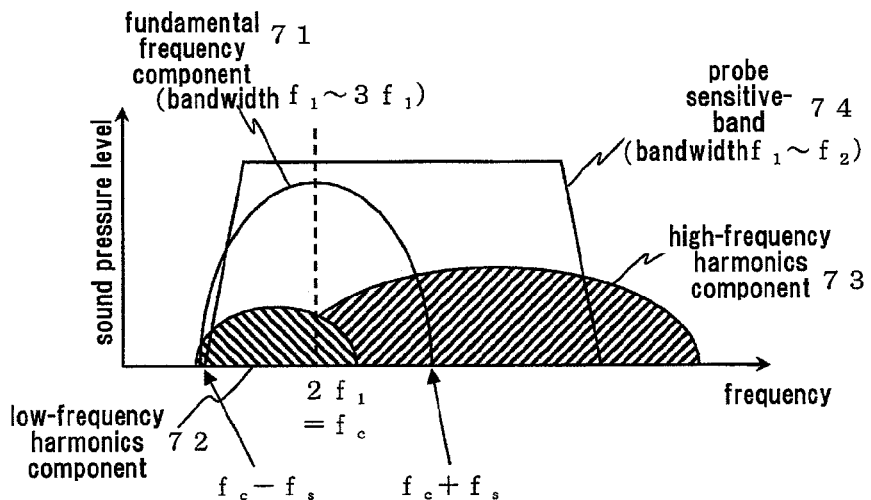
Figure 5:
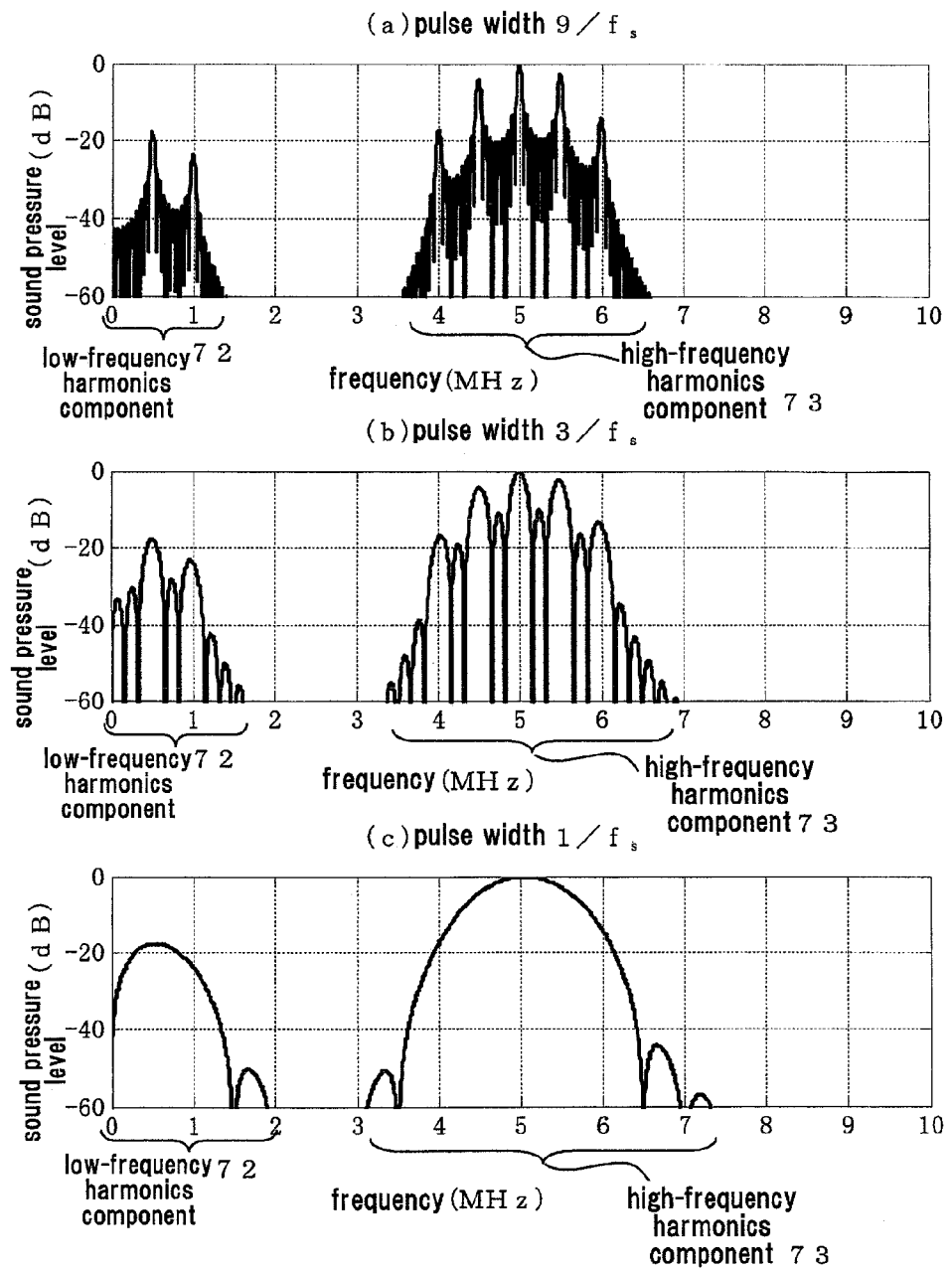
Figure 7:
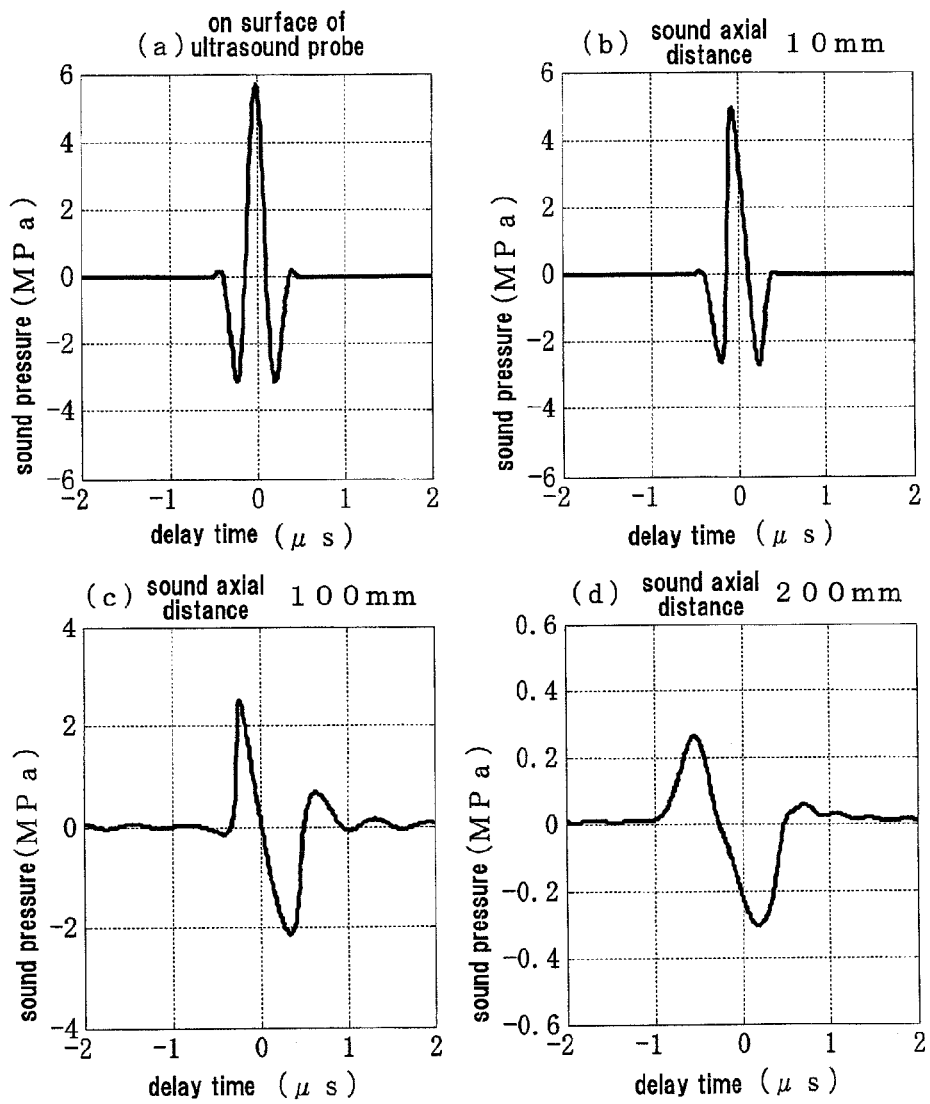
Figure 8:
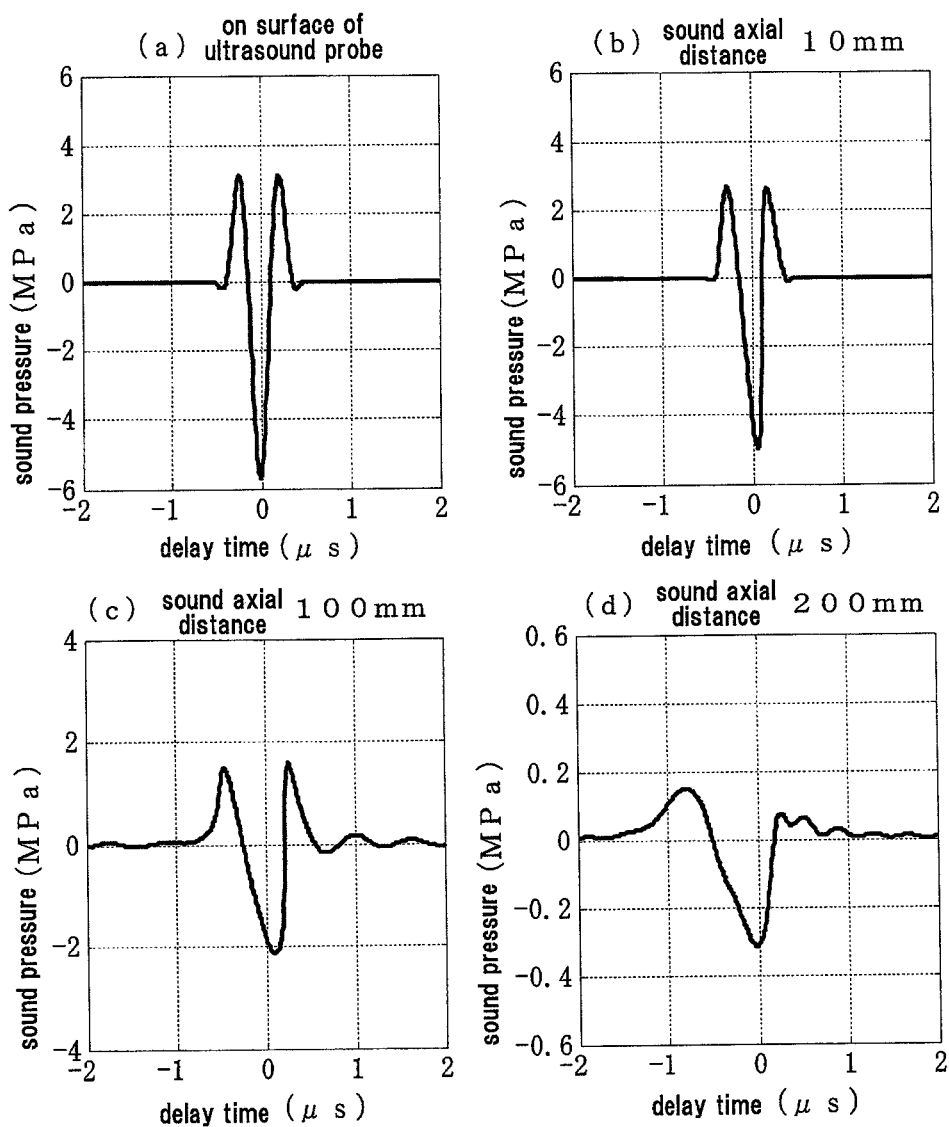
Figure 9:
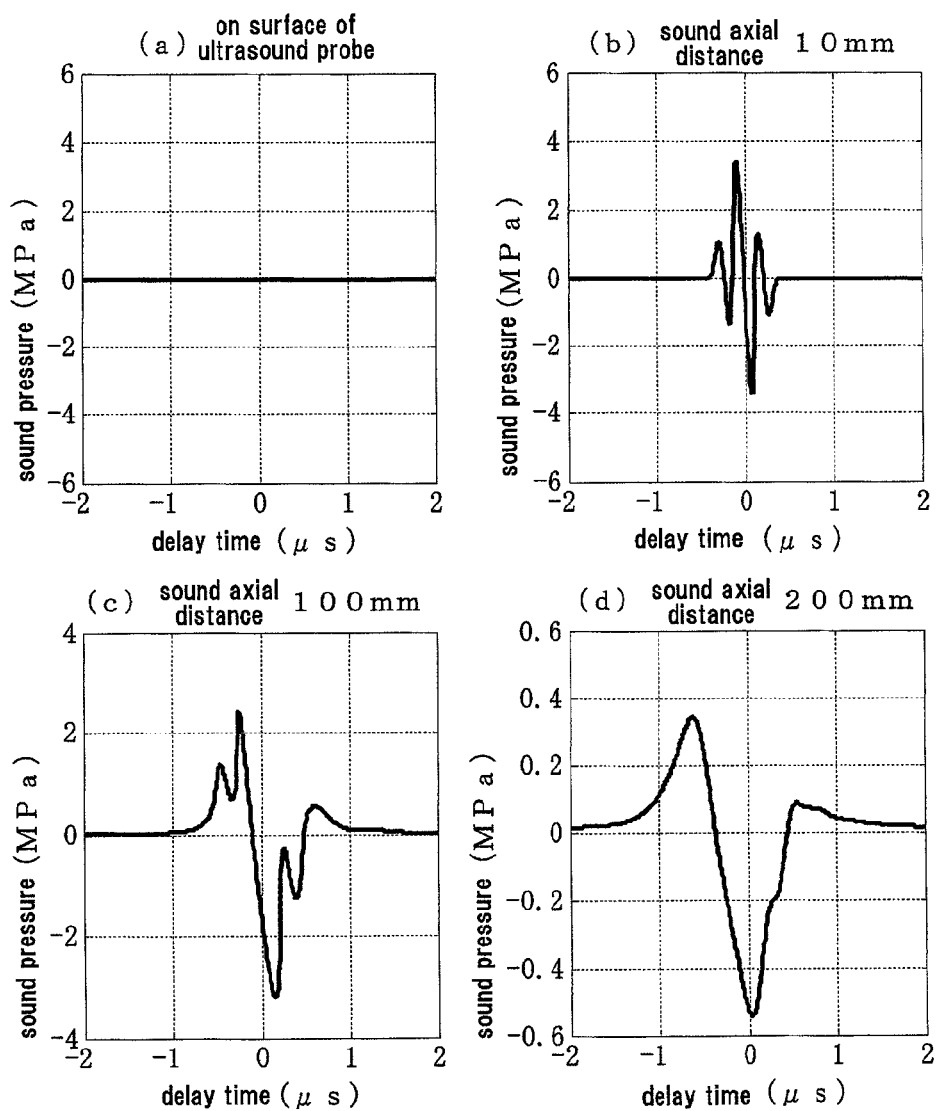
Figure 10:
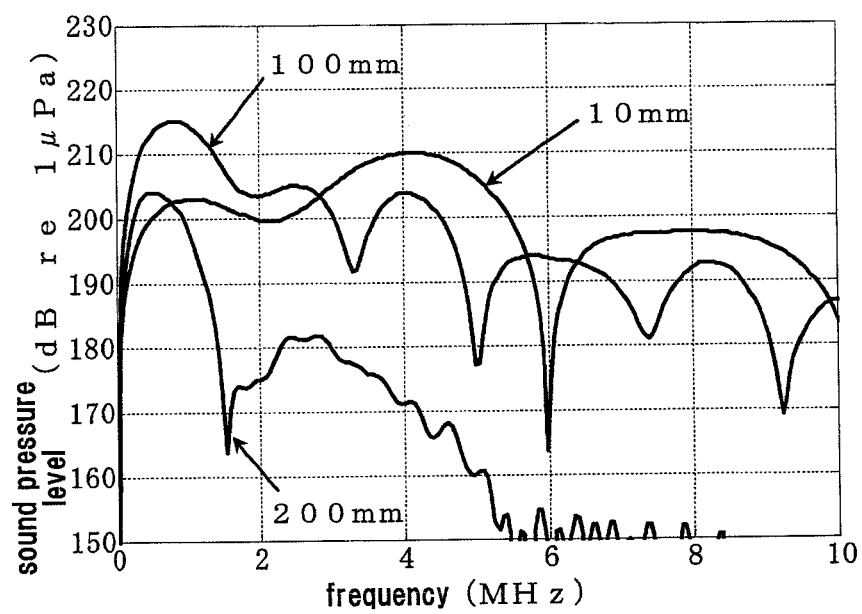
Figure 11:
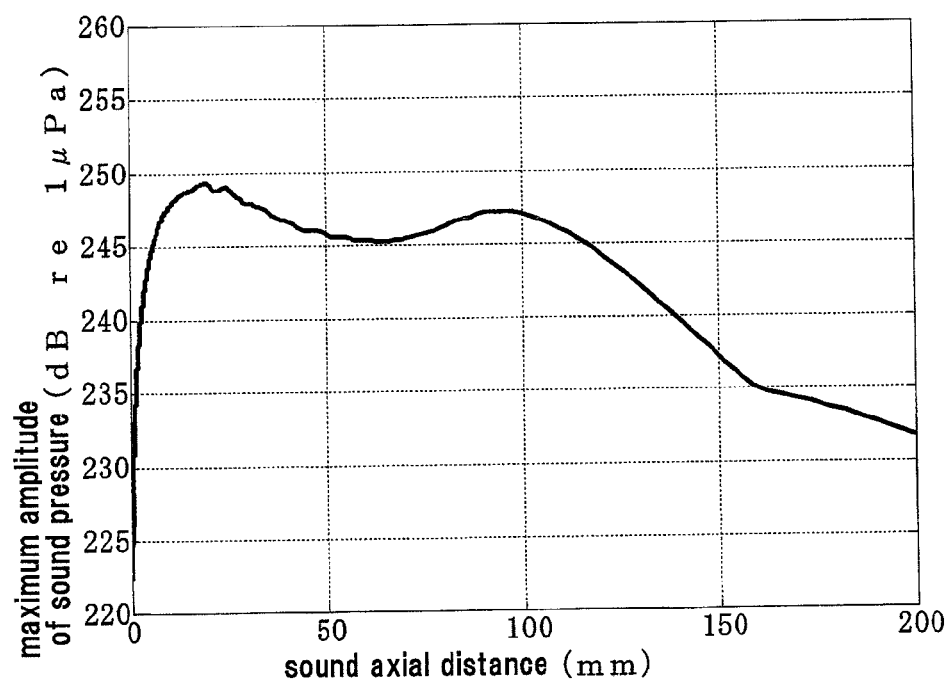
Figure 12:
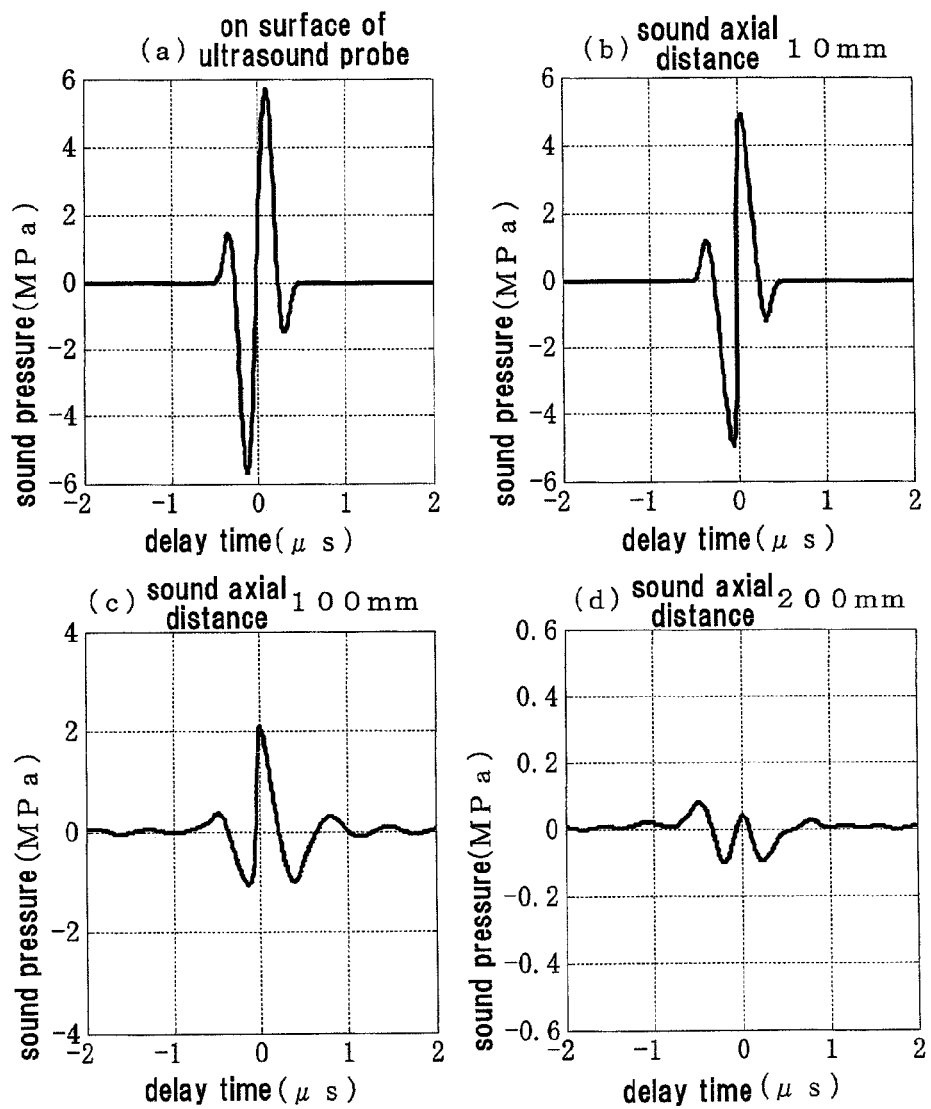
Figure 13:
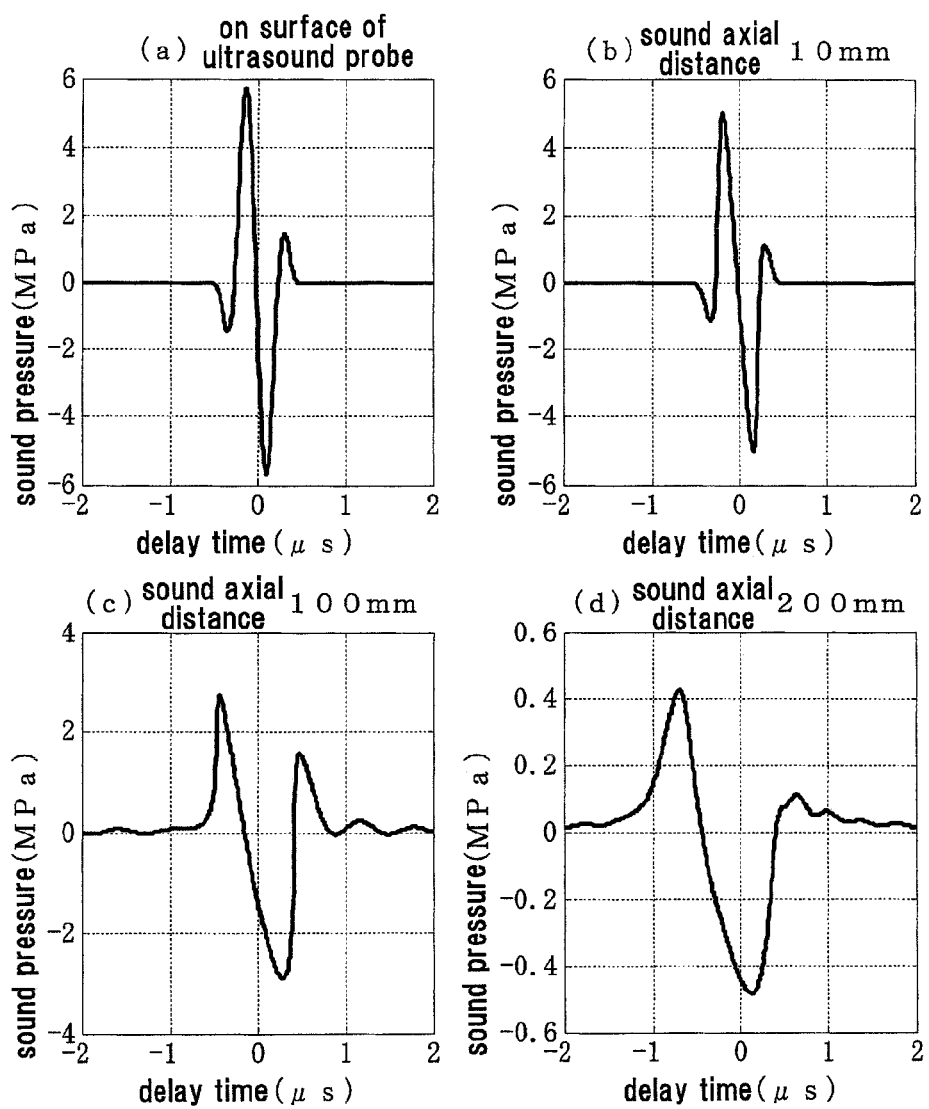
Figure 14:
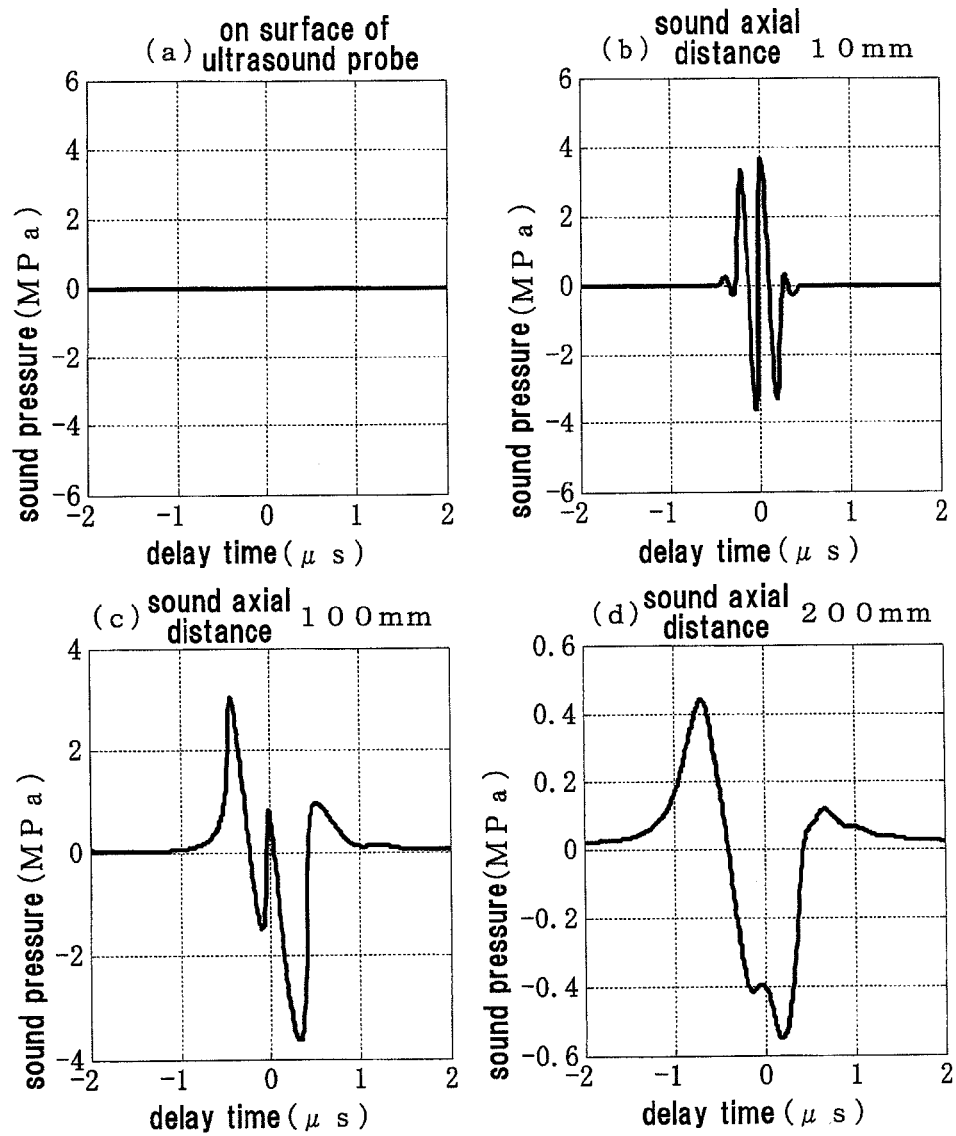
Figure 15:
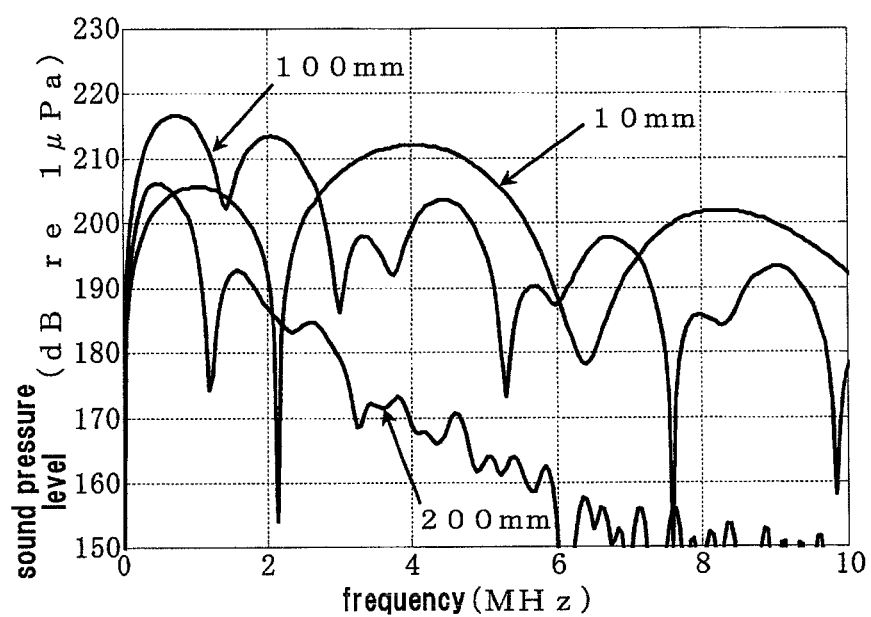
Figure 16:
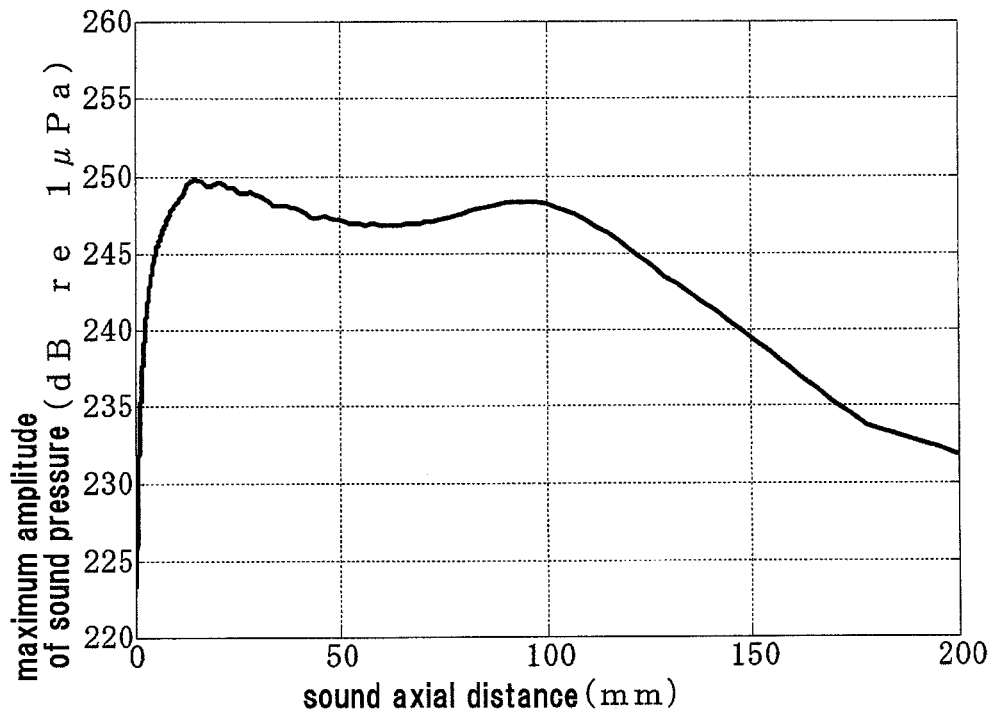
Figure 17:
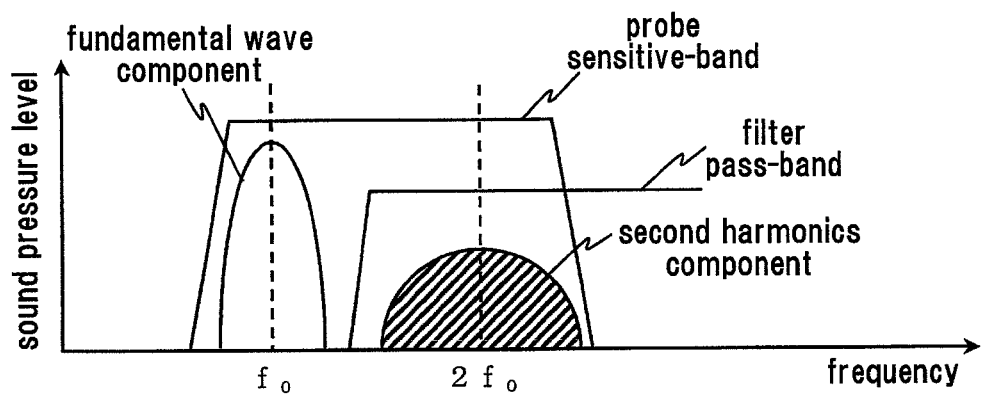
Figure 18:
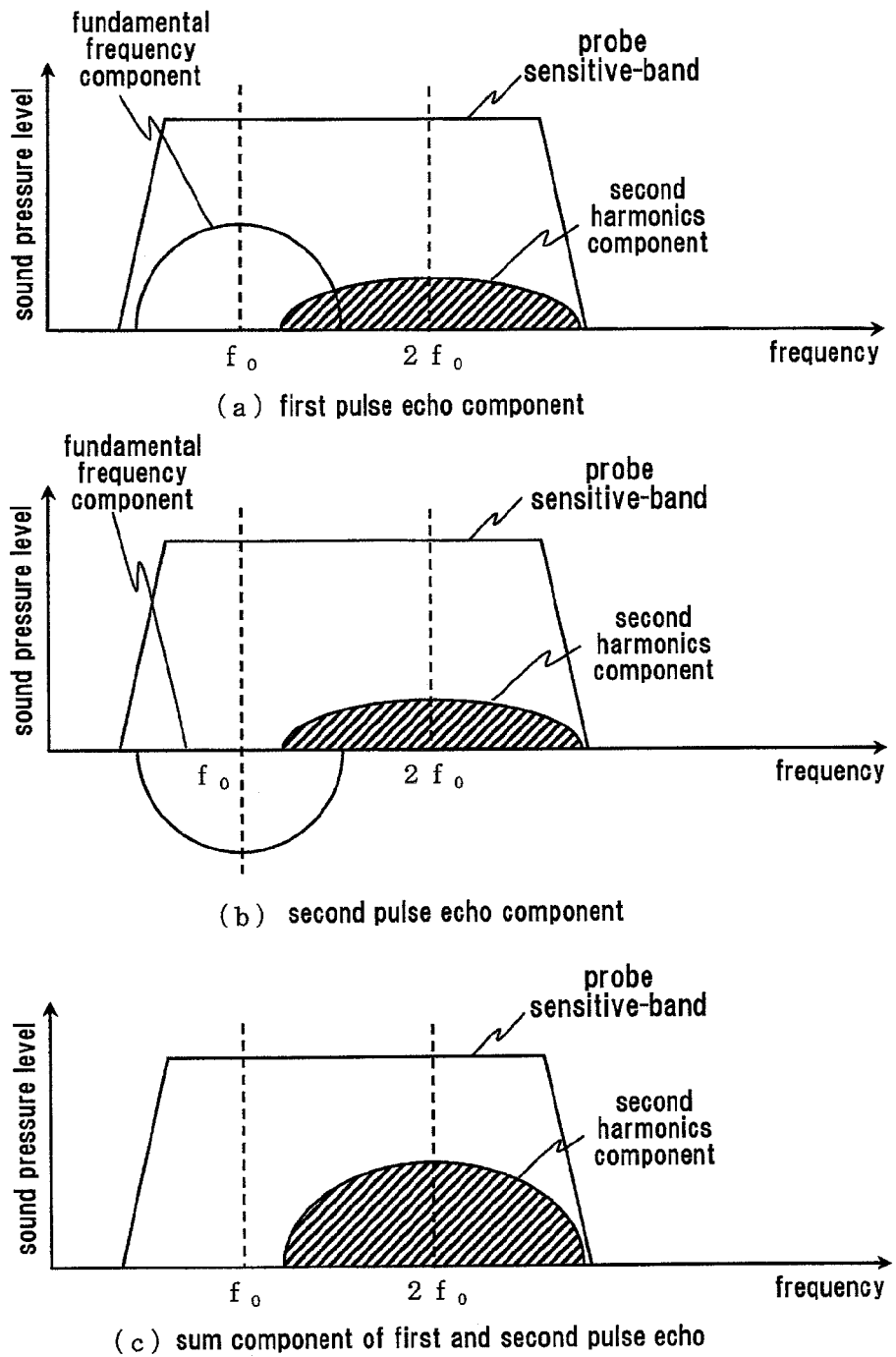
Figure 19:
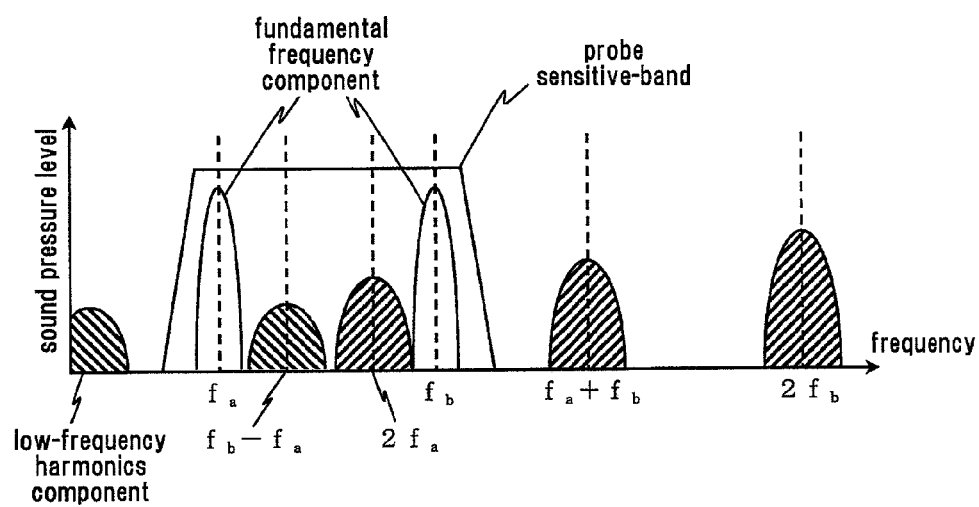

10 Ultrasound diagnostic equipment
11 Ultrasound probe
12 Outer interface
13 Display
20 Main frame
21 Transmit/Receive switch
22 Transmit amplifier
23 Pulse synchronizer
24 Receive amplifier 25 A/D converter
26 Receive beamformer
27 Signal processor
28 Imaging processor
29 Controller
30 First fundamental wave pulse
31 First received echo
32 First received signal
33 Second fundamental wave pulse
34 Second received echo
35 Second received signals
40,41 Temporary memory
42 Adder
43 Quadrature detecting processor
44 Filtering processor
45 B-mode processor
46 Doppler processor

The invention claimed is:

1. An ultrasound imaging apparatus, comprising a transmitter which transmits a fundamental wave pulse an to a subject, a receiver which receives an echo in response to the fundamental wave pulse from the subject, and a signal processor to process a received signal at the receiver and generate image data, wherein the receiver has a predetermined reception band, wherein the fundamental wave pulse transmitted by the transmitter consists of one frequency band having a frequency peak that includes fundamental wave components, and each of an upper limit frequency and a lower limit frequency of the one frequency band is set to be values which make both of a low frequency harmonic component and a high frequency harmonic component be generated within the reception band by a nonlinear acoustic overlap between the low and high frequency harmonic components within a bandwidth of the transmitted fundamental frequency component, where the lower and higher frequency component bands are different from the fundamental frequency component band; and wherein the signal processor generates image data by using nonlinear components including both of a nonlinear component of at least one of the low frequency harmonic component and the high frequency harmonic component received by the receiver.

2. The ultrasound imaging apparatus according to claim 1, wherein the transmitter transmits, as the fundamental wave pulse, a first ultrasound wave with the one frequency band and a second ultrasound wave with the one frequency band and having an inverted waveform of the first ultrasound wave, and wherein the signal processor adds a first received signal received by the receiver, which is an ultrasound wave originating from the first ultrasound wave and comes from the subject, and a second received signal received by the receiver, which is an ultrasound wave originating from the second ultrasound wave and comes from the subject, and generates image data by using added signals.

3. The ultrasound imaging apparatus according to claim 1, wherein the wave pulse of one frequency band has a lower limit of at least a first frequency and an upper limit of at least triple the first frequency.

* * * * *